United States Patent
Ianchulev et al.

(10) Patent No.: US 12,310,892 B2
(45) Date of Patent: May 27, 2025

(54) METHODS AND DEVICES FOR INCREASING AQUEOUS DRAINAGE OF THE EYE

(71) Applicant: Iantrek, Inc., Harrison, NY (US)

(72) Inventors: Tsontcho Ianchulev, Harrison, NY (US); David Robson, Harrison, NY (US)

(73) Assignee: Iantrek, Inc., Harrison, NY (US)

( * ) Notice: Subject to any disclaimer, the term of this patent is extended or adjusted under 35 U.S.C. 154(b) by 350 days.

(21) Appl. No.: 17/941,307

(22) Filed: Sep. 9, 2022

(65) Prior Publication Data

US 2023/0082713 A1 Mar. 16, 2023

Related U.S. Application Data

(60) Provisional application No. 63/344,443, filed on May 20, 2022, provisional application No. 63/254,436, filed on Oct. 11, 2021, provisional application No. 63/242,856, filed on Sep. 10, 2021.

(51) Int. Cl.
*A61F 9/007* (2006.01)

(52) U.S. Cl.
CPC .. *A61F 9/00781* (2013.01); *A61F 2210/0014* (2013.01); *A61F 2240/001* (2013.01)

(58) Field of Classification Search
CPC ...... A61B 17/3211; A61B 2017/00867; A61B 2017/320082; A61B 2017/3454; A61F 9/00781; A61F 9/007; A61F 9/00736; A61F 9/00745; A61F 9/0133; A61F 2250/0013;
(Continued)

(56) References Cited

U.S. PATENT DOCUMENTS

| 5,437,678 A | 8/1995 | Sorensen |
|---|---|---|
| 6,979,328 B2 | 12/2005 | Baerveldt et al. |
| 7,207,980 B2 | 4/2007 | Christian et al. |

(Continued)

FOREIGN PATENT DOCUMENTS

| CN | 101360523 A | 2/2009 |
|---|---|---|
| CN | 102824238 A | 12/2012 |

(Continued)

OTHER PUBLICATIONS

Sun, X. H., Wang, Y., & Meng, F. R. (2003). [Zhonghua yan ke za zhi] Chinese Journal of Ophthalmology, 39(8), 462-465. [English language abstract].

(Continued)

*Primary Examiner* — Katherine M Shi
(74) *Attorney, Agent, or Firm* — Mintz Levin Cohn Ferris Glovsky and Popeo, P.C.

(57) ABSTRACT

A device for disrupting tissue in an eye including a distal portion sized and configured for ab interno insertion into an anterior chamber of the eye having an elongate, flexible shaft of super-elastic memory-shape material. A distal end region is shaped into a curve having a radially inner surface connected to a radially outer surface by two lateral sides. The device has a tissue disruptor proximal of a distal-most end formed on at least one of the inner surface and the outer surface. The distal face of the tissue disruptor is a blunt tissue-engaging surface without any cutting element. Related methods and devices are provided.

18 Claims, 17 Drawing Sheets

(58) Field of Classification Search
CPC ............ A61F 2210/0014; A61F 9/0017; A61F 2009/00891
See application file for complete search history.

(56) References Cited

U.S. PATENT DOCUMENTS

| | | | |
|---|---|---|---|
| 7,465,310 B2 | 12/2008 | Isogimi |
| 7,699,882 B2 | 4/2010 | Stamper et al. |
| 7,785,321 B2 | 8/2010 | Baerveldt et al. |
| 7,842,034 B2 | 11/2010 | Mittelstein et al. |
| 7,959,641 B2 | 6/2011 | Sorensen et al. |
| 7,967,772 B2 | 6/2011 | McKenzie et al. |
| 8,034,105 B2 | 10/2011 | Stegmann et al. |
| 8,123,729 B2 | 2/2012 | Yamamoto et al. |
| 8,172,830 B2 | 5/2012 | Christian et al. |
| 8,267,882 B2 | 9/2012 | Euteneuer et al. |
| 8,348,924 B2 | 1/2013 | Christian et al. |
| 8,425,473 B2 | 4/2013 | Ho et al. |
| 8,491,549 B2 | 7/2013 | Conston et al. |
| 8,512,321 B2 | 8/2013 | Baerveldt et al. |
| 8,529,494 B2 | 9/2013 | Euteneuer et al. |
| 8,721,656 B2 | 5/2014 | De Juan, Jr. et al. |
| 8,894,603 B2 | 11/2014 | Badawi et al. |
| 9,066,783 B2 | 6/2015 | Euteneuer et al. |
| 9,095,412 B2 | 8/2015 | Badawi et al. |
| 9,107,729 B2 | 8/2015 | Sorensen et al. |
| 9,216,109 B2 | 12/2015 | Badawi et al. |
| 9,226,850 B2 | 1/2016 | Baerveldt et al. |
| 9,358,155 B2 | 6/2016 | Sorensen et al. |
| 9,693,902 B2 | 7/2017 | Euteneuer et al. |
| 9,757,279 B2 | 9/2017 | Kahook |
| 9,820,883 B2 | 11/2017 | Berlin |
| 9,820,885 B2 | 11/2017 | Sorensen et al. |
| 9,855,167 B2 | 1/2018 | Badawi et al. |
| 9,872,799 B2 | 1/2018 | Kahook |
| 9,895,258 B2 | 2/2018 | Badawi et al. |
| 9,999,544 B2 | 6/2018 | Baerveldt et al. |
| 10,085,885 B2 | 10/2018 | Baerveldt et al. |
| 10,123,905 B2 | 11/2018 | Mittelstein et al. |
| 10,179,066 B2 | 1/2019 | Badawi et al. |
| 10,327,947 B2 | 6/2019 | Kahook |
| 10,695,218 B1 | 6/2020 | Ianchulev |
| 10,905,591 B1 | 2/2021 | Ianchulev |
| 11,419,762 B2 | 8/2022 | Ianchulev |
| 2003/0236484 A1 | 12/2003 | Lynch et al. |
| 2006/0047263 A1 | 3/2006 | Tu et al. |
| 2006/0241580 A1 | 10/2006 | Mittelstein et al. |
| 2007/0073275 A1 | 3/2007 | Conston et al. |
| 2008/0228127 A1 | 9/2008 | Burns et al. |
| 2009/0287143 A1 | 11/2009 | Line |
| 2009/0287233 A1 | 11/2009 | Huculak |
| 2010/0262174 A1 | 10/2010 | Sretavan et al. |
| 2010/0280317 A1 | 11/2010 | Silvestrini et al. |
| 2012/0035524 A1 | 2/2012 | Silvestrini |
| 2012/0083727 A1 | 4/2012 | Barnett |
| 2012/0191064 A1 | 7/2012 | Conston et al. |
| 2013/0184631 A1 | 7/2013 | Pinchuk |
| 2013/0253402 A1 | 9/2013 | Badawi et al. |
| 2013/0253403 A1 | 9/2013 | Badawi et al. |
| 2013/0289545 A1 | 10/2013 | Baerveldt et al. |
| 2015/0045820 A1 | 2/2015 | Kahook |
| 2015/0080783 A1 | 3/2015 | Berlin |
| 2016/0100980 A1 | 4/2016 | Badawi et al. |
| 2016/0287438 A1 | 10/2016 | Badawi et al. |
| 2017/0252212 A1 | 9/2017 | Euteneuer et al. |
| 2017/0258636 A1 | 9/2017 | Baerveldt et al. |
| 2017/0367890 A1 | 12/2017 | Kahook |
| 2018/0125712 A1 | 5/2018 | Sorensen et al. |
| 2018/0133056 A1 | 5/2018 | Kahook |
| 2018/0147088 A1 | 5/2018 | Liang et al. |
| 2018/0271699 A1 | 9/2018 | Badawi et al. |
| 2018/0289544 A1 | 10/2018 | Baerveldt et al. |
| 2018/0360655 A1 | 12/2018 | Berlin |
| 2018/0360661 A1 | 12/2018 | Kahook et al. |
| 2019/0060119 A1 | 2/2019 | Baerveldt et al. |
| 2019/0076296 A1 | 3/2019 | Ivantis |
| 2019/0142632 A1 | 5/2019 | Badawi et al. |
| 2020/0390601 A1 | 12/2020 | Ianchulev |
| 2020/0390602 A1 | 12/2020 | Ianchulev |
| 2021/0022919 A1 | 1/2021 | Ianchulev |
| 2021/0361484 A1 | 11/2021 | Ianchulev |
| 2022/0387215 A1* | 12/2022 | Filice ................. A61B 10/0275 |
| 2023/0000680 A1 | 1/2023 | Ianchulev et al. |

FOREIGN PATENT DOCUMENTS

| | | |
|---|---|---|
| CN | 103932840 A | 7/2014 |
| CN | 104203153 A | 12/2014 |
| CN | 105530875 A | 4/2016 |
| CN | 205359780 U | 7/2016 |
| CN | 107530190 A | 1/2018 |
| CN | 109195536 A | 1/2019 |
| WO | WO-00/64389 A1 | 11/2000 |
| WO | WO-2011/106781 A1 | 9/2011 |
| WO | WO-2016/044672 A1 | 3/2016 |
| WO | WO-2016/159999 A1 | 10/2016 |
| WO | WO-2020/120455 A1 | 6/2020 |

OTHER PUBLICATIONS

U.S. Appl. No. 16/777,648, filed Jan. 30, 2020, US 20200390601 A1.
U.S. Appl. No. 17/178,066, filed Feb. 17, 2021, US 20210196516 A1.
U.S. Appl. No. 17/325,785, filed May 20, 2021, US 20210361484 A1.
PCT/US21/33335, May 20, 2021, WO 2021/236892.
U.S. Appl. No. 17/865,059, filed Jul. 14, 2022, US 20230009442 A1.
U.S. Appl. No. 17/940,380, filed Sep. 8, 2022, US 20230000680 A1.
U.S. Appl. No. 18/430,141, filed Feb. 1, 2024, US 20240164943 A1.
PCT/US2023/80677, Nov. 21, 2023, WO 2024/112747.

* cited by examiner

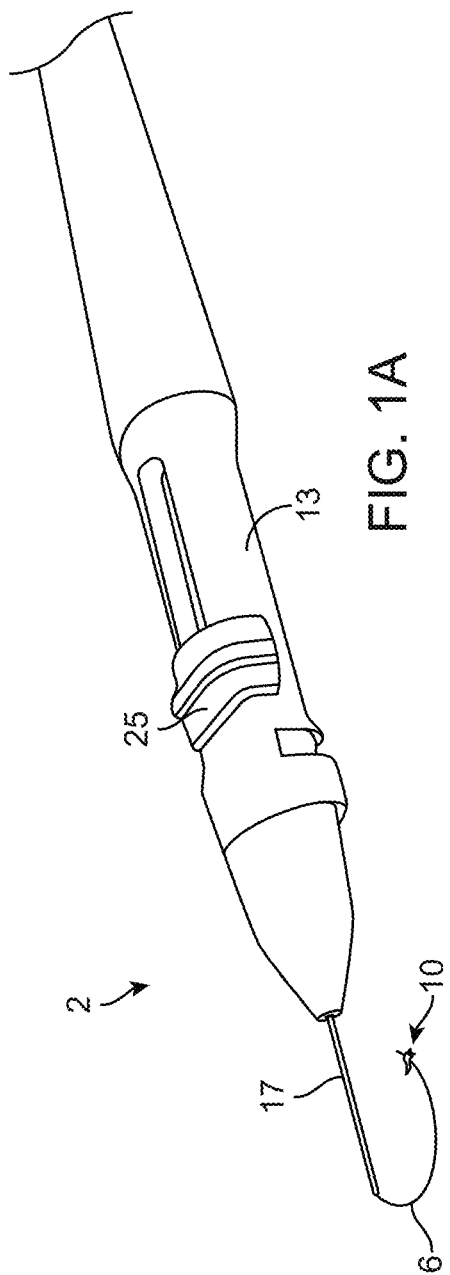
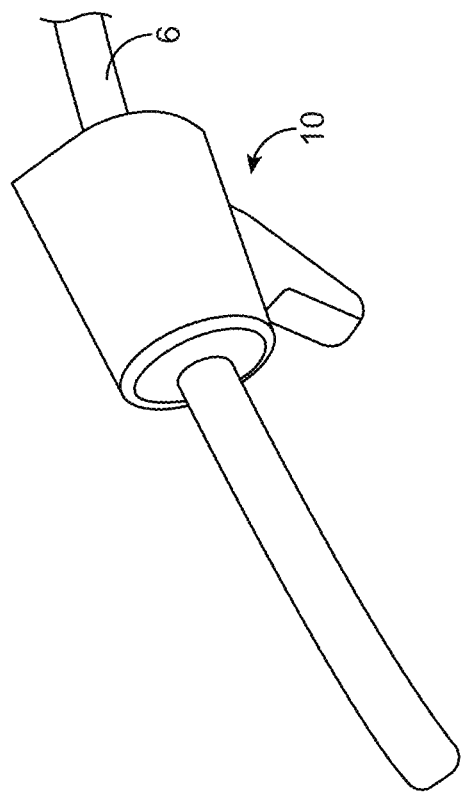
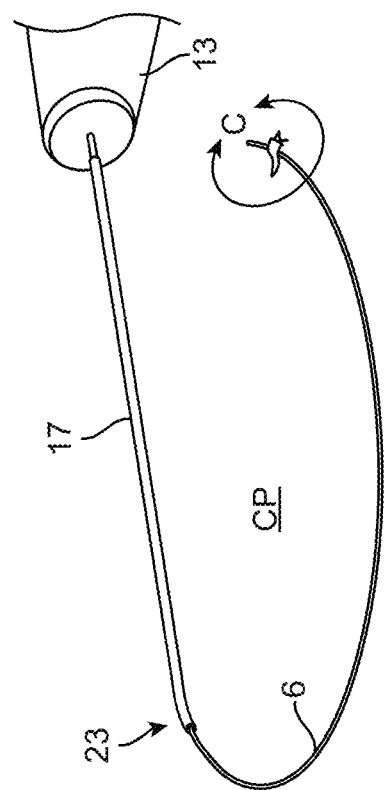
FIG. 1A
FIG. 1B
FIG. 1C

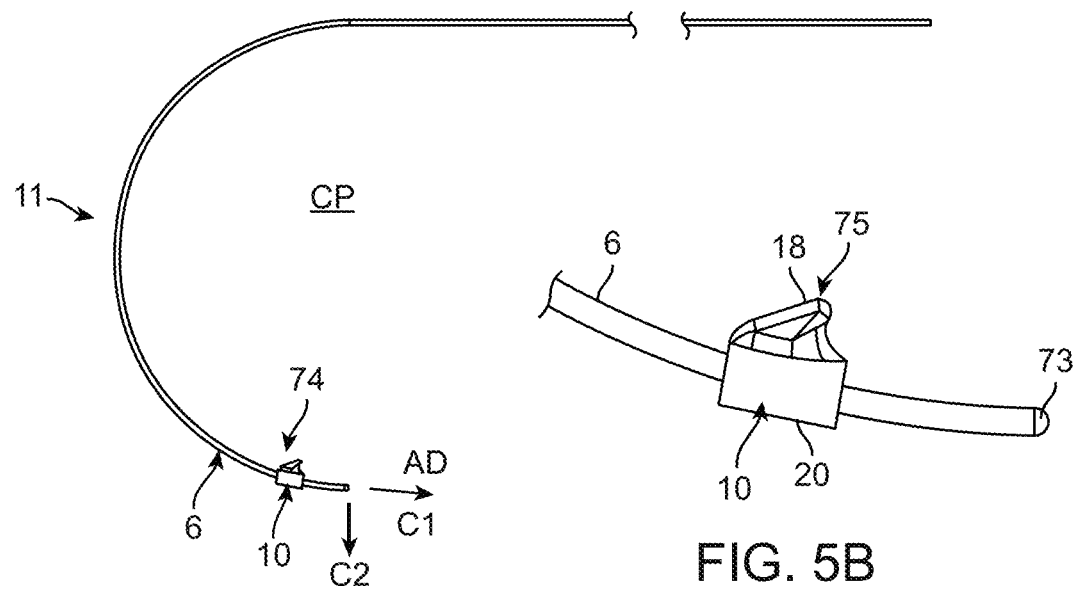
FIG. 5A
FIG. 5B
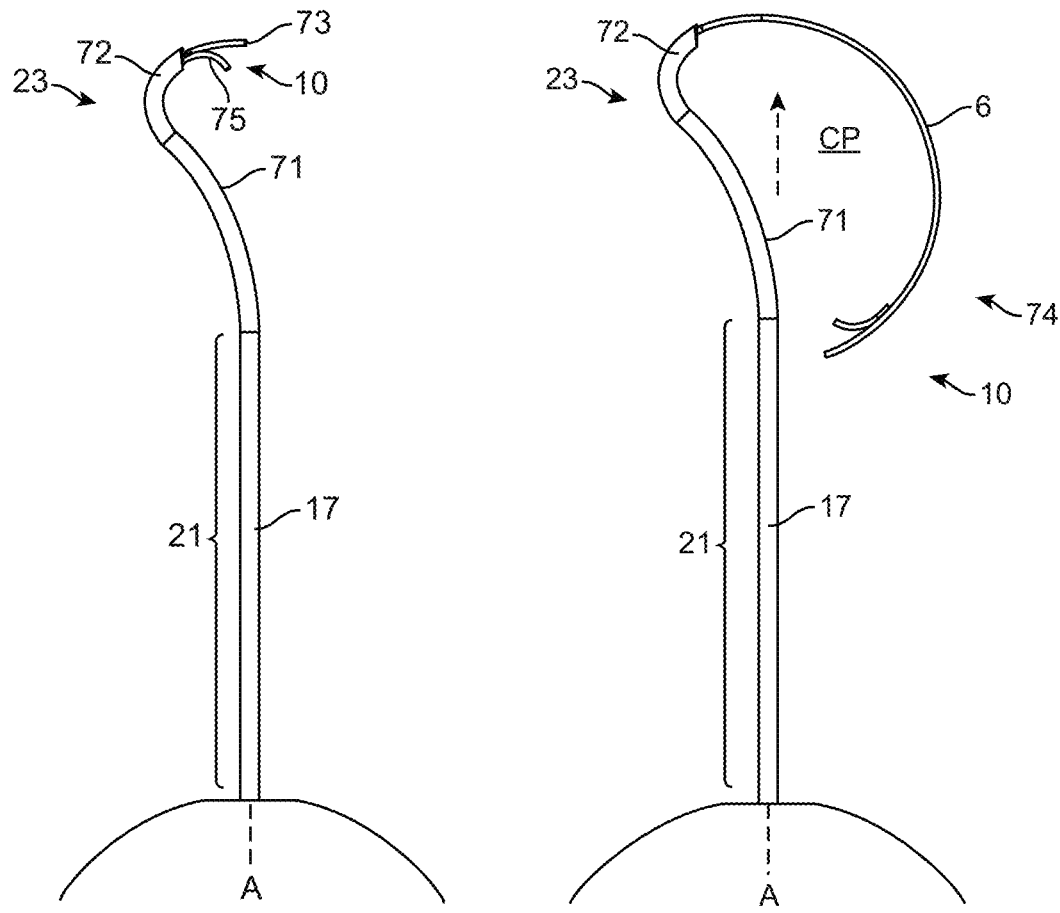
FIG. 6A
FIG. 6B

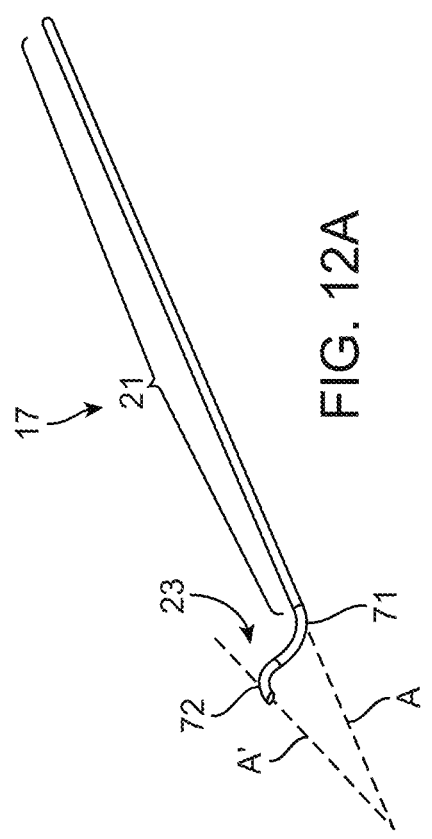
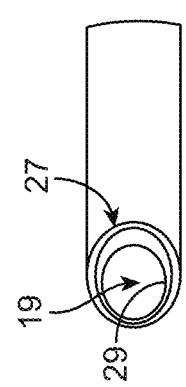
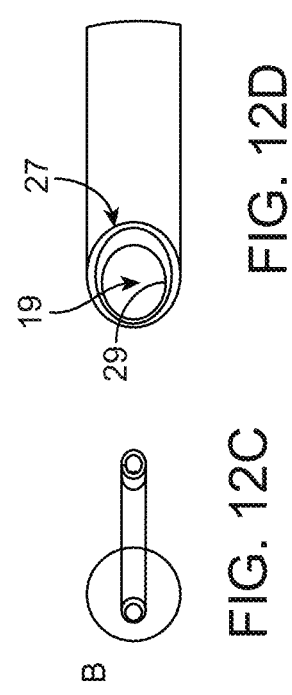
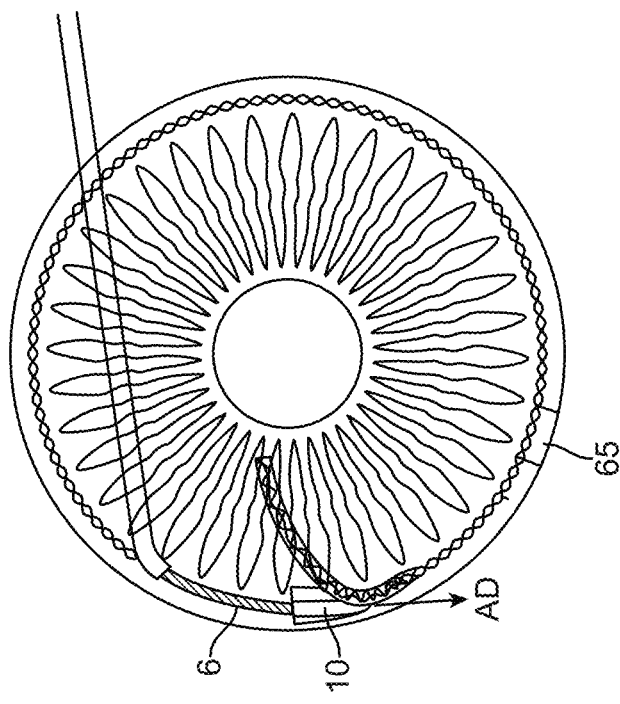
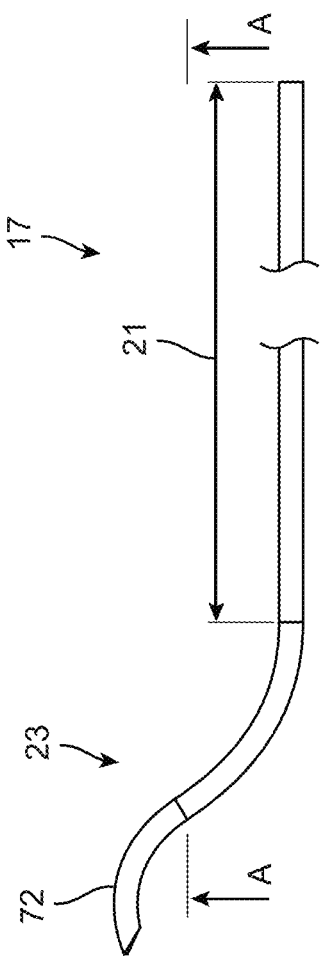
FIG. 12A
FIG. 12D
FIG. 12C
FIG. 11
FIG. 12B

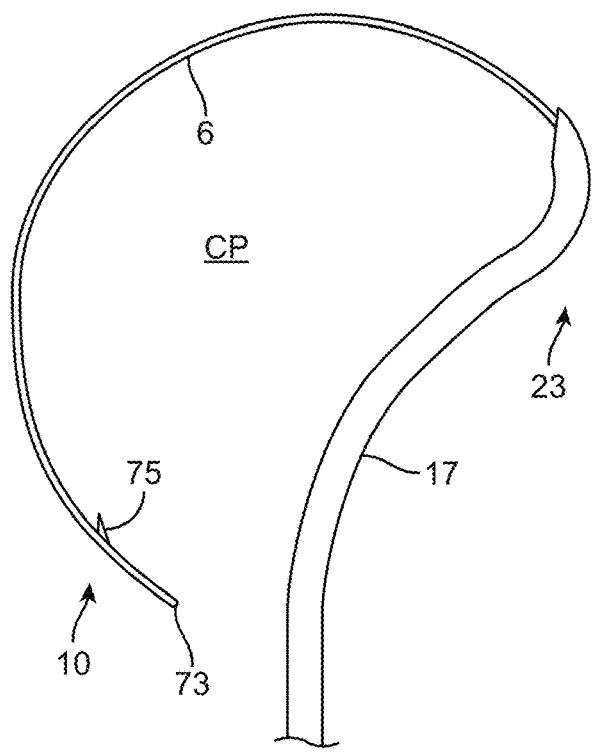
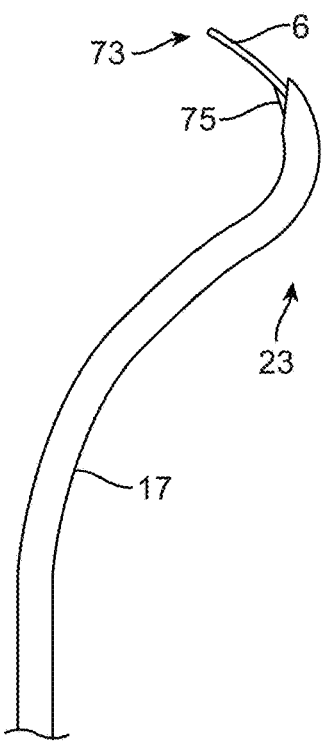
FIG. 14A  FIG. 14B
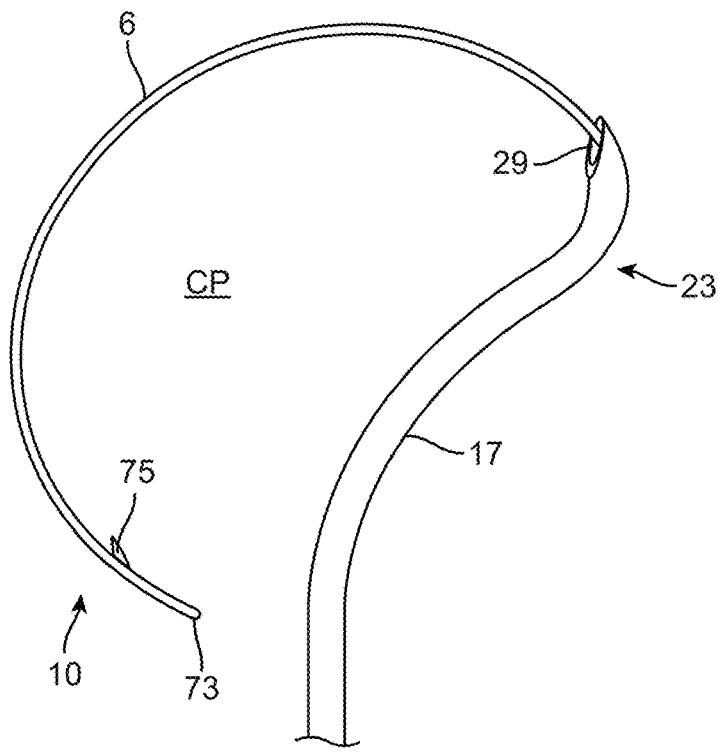
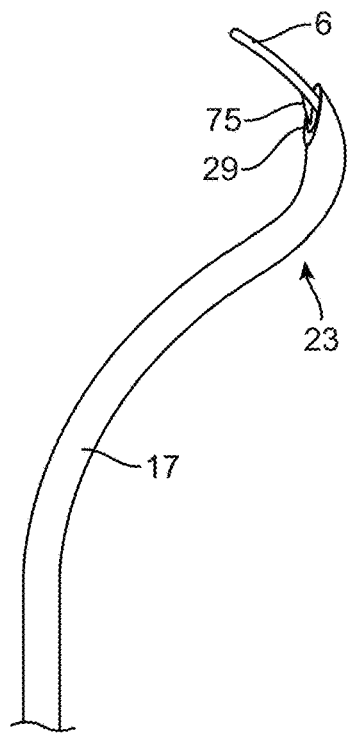
FIG. 14C  FIG. 14D

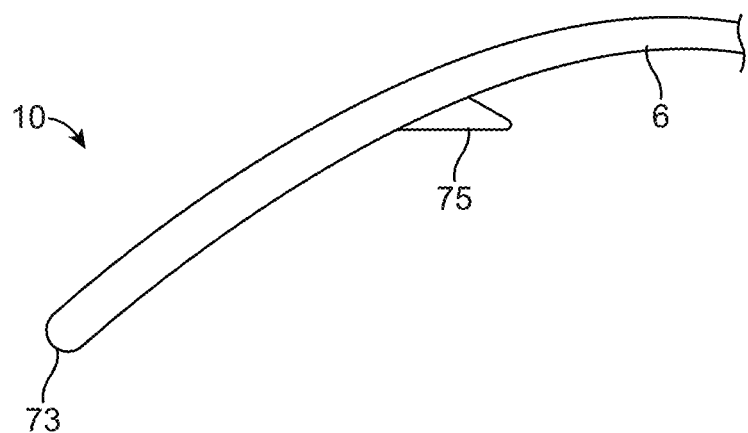
FIG. 14E
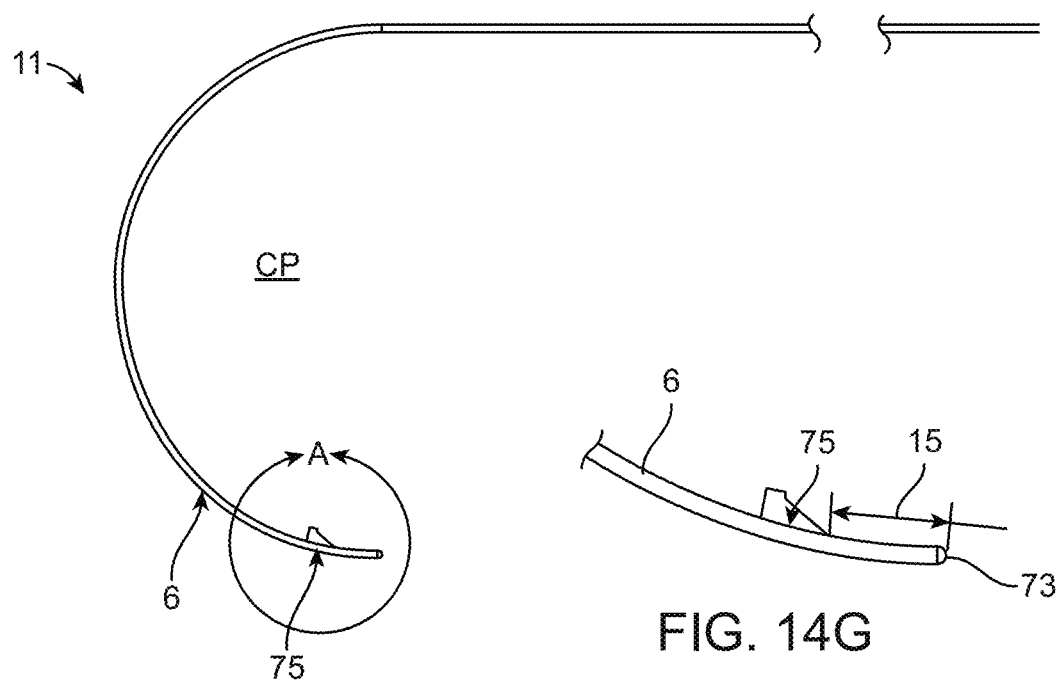
FIG. 14F
FIG. 14G

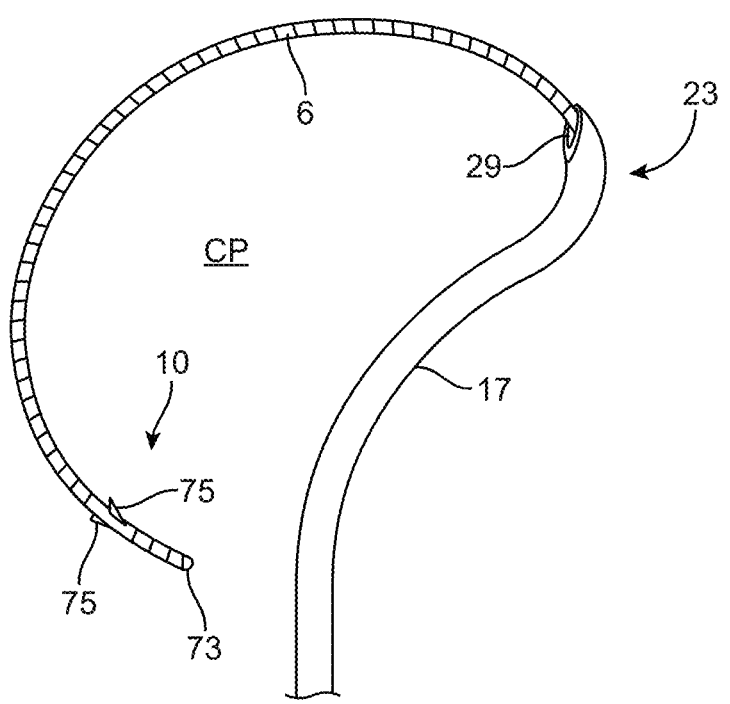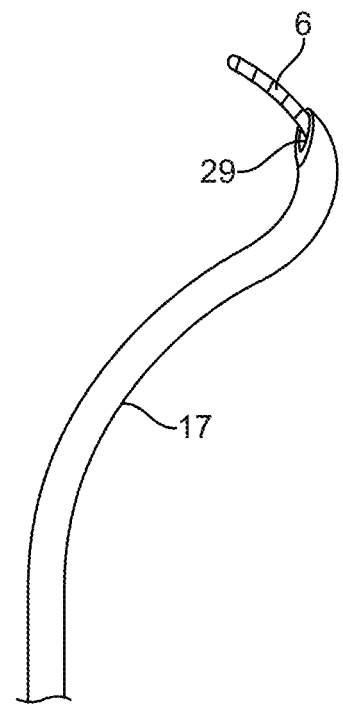
FIG. 16C  FIG. 16D
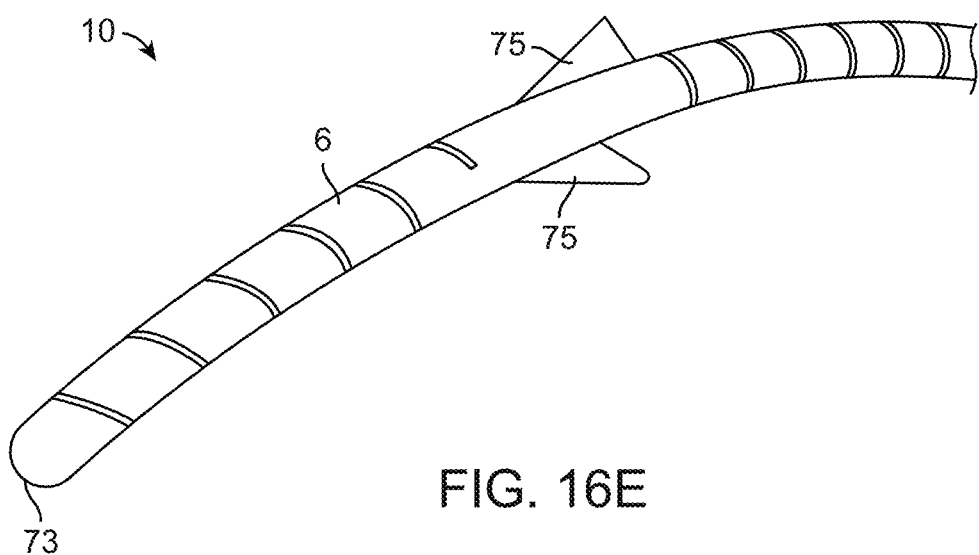
FIG. 16E

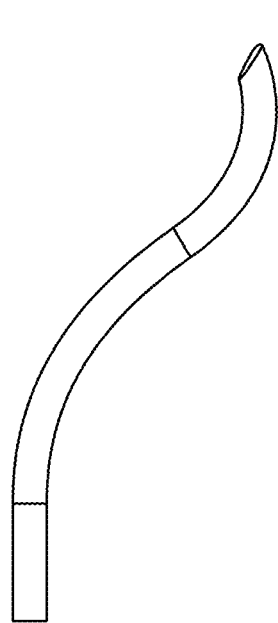 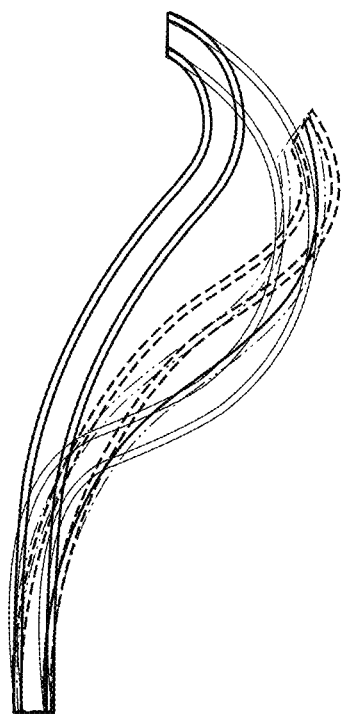
FIG. 17A  FIG. 17B
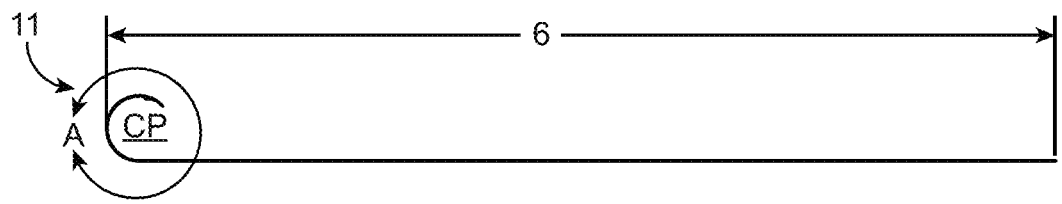
FIG. 18A
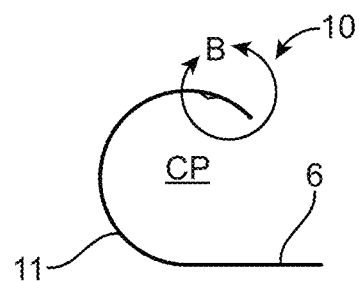 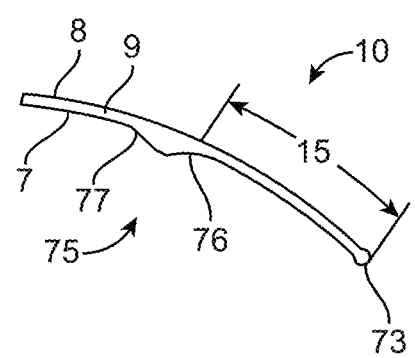
FIG. 18B  FIG. 18C

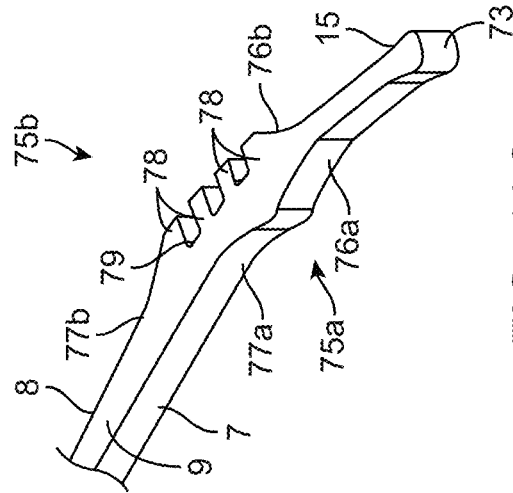
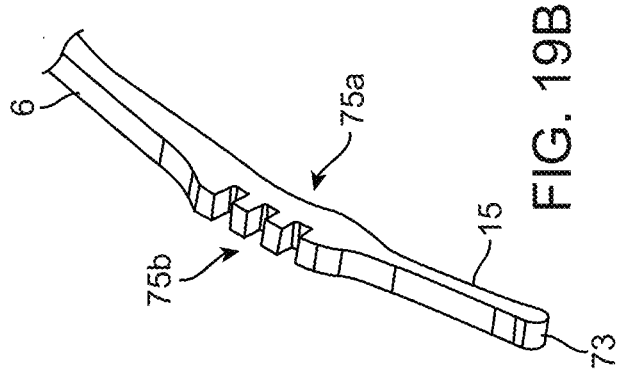
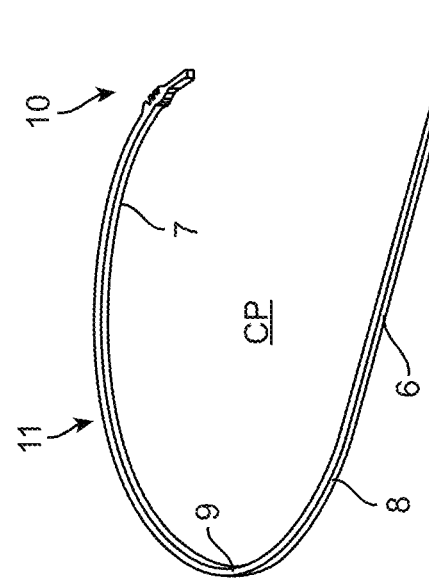
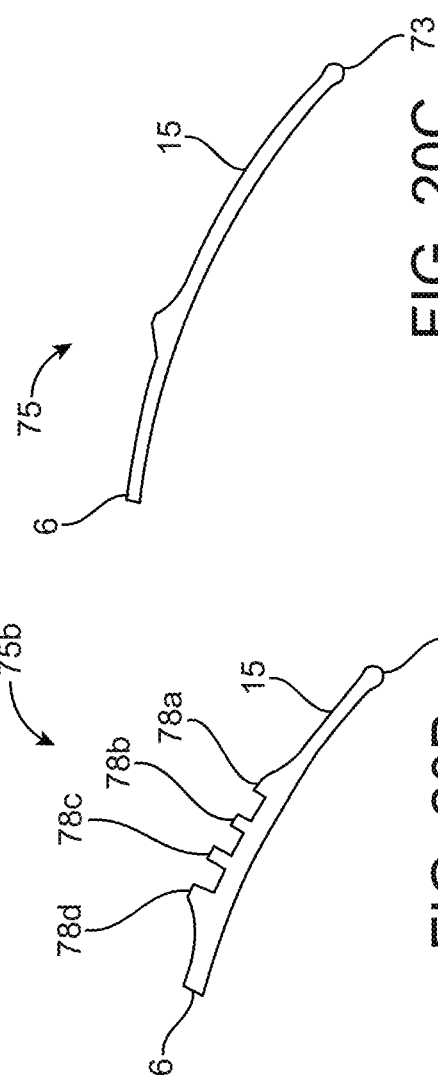
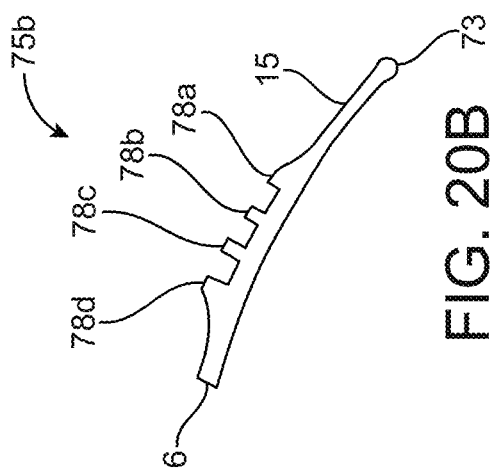
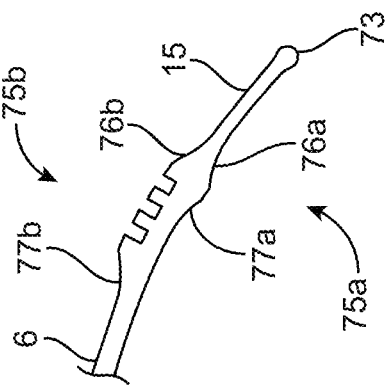

METHODS AND DEVICES FOR INCREASING AQUEOUS DRAINAGE OF THE EYE

CROSS-REFERENCE TO RELATED APPLICATIONS

This application claims the benefit of priority under 35 U.S.C. § 119(e) to Provisional Patent Application Ser. No. 63/242,856 filed Sep. 10, 2021, Provisional Patent Application Ser. No. 63/254,436 filed Oct. 11, 2021, and Provisional Patent Application Ser. No. 63/344,443, filed May 20, 2022. The disclosures of the provisional applications are incorporated by reference in their entireties.

BACKGROUND

Current trabecular excision devices typically use excisional blades or sharp needles (e.g. goniotomy). These devices typically create single stab-like partial cuts of the trabecular meshwork. More recent devices, such as the Kahook dual blade (U.S. Pat. No. 9,872,799), Baervelt (U.S. Pat. No. 9,999,544) and the cauterizing/plasma cutting blades of the Trabectome (U.S. Pat. No. 9,820,885), all have a sharp incisional or ablative cutting surface for use on the trabecular meshwork. As such, they all suffer from the major clinical disadvantage related to the sharp cutting nature in the process of meshwork engagement. The sharp blades often create interrupted, discontinuous and incongruous cuts of the trabecular meshwork, which are imprecise and more akin to tissue maceration rather than the desired tissue extraction with non-lacerating atraumatic removal. This is also often associated with significant bleeding and collateral damage of both sclera, endothelium and iris tissue. Furthermore, a single cutting blade may simply open the trabecular meshwork without removing much material. In order to remove material, some prior art devices provide two spaced-apart cutting elements (side-by-side) in an attempt to remove meshwork material between the cutting elements.

SUMMARY

In an aspect, described is a device for disrupting tissue in an eye including a distal portion sized and configured for ab interno insertion into an anterior chamber of the eye. The distal portion has an elongate, flexible shaft of super-elastic memory-shape material including a distal end region shaped into a curve having a central plane. A radially inner surface is connected to a radially outer surface by two lateral sides. The shaft includes a distal-most end; and a tissue disruptor proximal of the distal-most end formed on at least one of the inner surface and the outer surface. The tissue disruptor has a distal face, a proximal face, and a maximum thickness, the distal face sloping from a first thickness of the shaft distal to the tissue disruptor towards the maximum thickness and the proximal face tapering down from the maximum thickness to a second thickness of the shaft proximal to the tissue disruptor. The first thickness, the maximum thickness, and the second thickness are each between the inner and outer surfaces. The distal face of the tissue disruptor is a blunt tissue-engaging surface without any cutting element.

The distal-most end can be a smooth ball tip. The smooth ball tip is configured for circumferential gonio-traction. The smooth ball tip on the shaft can be located 1 mm-3 mm away from the distal face. The tissue disruptor can include a first tissue disruptor formed on the inner surface and a second tissue disruptor formed on or adjacent to the outer surface opposite the first tissue disruptor. The second tissue disruptor can include a plurality of teeth and a distal face sloping from the first thickness of the shaft to a first tooth of the plurality of teeth. The device can further include a proximal housing having an introducer tube projecting from a distal end region of the housing, at least a portion of the shaft extending through a lumen of the introducer tube. The shaft can be configured to be advanced from the introducer tube. The shaft can develop a spring-load as the shaft extends from the introducer tube. The shaft can apply a radially outward force as the shaft extends from the introducer tube. A stiffness of the shaft can be varied by changing a length of the shaft extending from the introducer tube.

The introducer tube can be a substantially rigid tube having a proximal end region that extends away from the proximal housing along a longitudinal axis and a distal end region that curves relative to the longitudinal axis. The distal end region of the introducer tube can have a first curved region and a second curved region. The first curved region can curve in a first direction at a first radius of curvature and the second curved region can curve in a second direction at a second radius of curvature. The first and second curved regions can combine to bring a tip of the introducer tube so it is nearly tangential with a curvature of Schlemm's Canal when in use. The first radius of curvature can be greater than the second radius of curvature. The first radius of curvature can be 2-9 mm and the second radius of curvature can be 1-4 mm. The first thickness of the shaft between the inner and outer surfaces proximal to the disruptor can be 100-150 microns and the second thickness of the shaft between the inner and outer surfaces distal to the disruptor can be 100-150 microns. The maximum thickness of the tissue disruptor between the inner and the outer surfaces can be about 250-600 microns. The first thickness of the shaft between the inner and outer surfaces proximal to the disruptor can be 100-2000 microns and the second thickness of the shaft between the inner and outer surfaces distal to the disruptor can be 100-550 microns. The maximum thickness of the tissue disruptor between the inner and the outer surfaces can be about 450-600 microns.

The shaft can have a cross-sectional shape taken transverse to a length of the shaft between that is non-circular. The cross-sectional shape can be square or rectangular. The super-elastic memory-shape material can be Nitinol. The shaft can be cut from a flat sheet of Nitinol having a thickness of about 75-550 microns to form a profile of the tissue disruptor.

The device can further include a proximal portion that is configured to remain outside the eye when the distal portion is inserted inside the eye. The proximal portion can include an actuator operatively coupled to the shaft, the actuator configured to advance the shaft distally. The curve of the distal end region of the shaft can have a radial curvature of 5-20 mm. The shaft can have a length sufficient to be advanced around 30-360 degrees of a circumference of an eye.

In an interrelated aspect, provided is a method of manufacturing a micro-interventional tool for use in Schlemm's canal or within an anterior angle of the eye including laser-shaping a flat sheet of super-elastic memory-shape material into an elongate, flexible shaft having a non-circular cross-section and a distal end region having a tissue disrupting profile.

The flat sheet can have a thickness that is 100-150 microns. The method can further include forming the distal end region into a curve having a central plane, wherein a radially inner surface is connected to a radially outer surface by two lateral sides. The tissue disrupting profile can include a tissue disruptor proximal of a distal-most end of the shaft on at least one of the inner surface and the outer surface. The tissue disruptor can have a distal face, a proximal face, and a maximum thickness, the distal face sloping from a first thickness of the shaft distal to the tissue disruptor towards the maximum thickness and the proximal face having a second thickness of the shaft proximal to the tissue disruptor, wherein the first thickness, the maximum thickness, and the second thickness are each between the inner and outer surfaces, and wherein the distal face of the tissue disruptor is a blunt surface without any cutting element. The tissue disrupting profile can further include a smooth ball tip on the distal-most end of the shaft. The smooth ball tip can be configured for circumferential gonio-traction. The smooth ball tip can be located 1 mm-3 mm away from the distal face. The tissue disruptor can include a first tissue disruptor formed on the inner surface and a second tissue disruptor formed on the outer surface opposite the first tissue disruptor. The second tissue disruptor can include a plurality of teeth and a distal face sloping from the first thickness of the shaft to a first tooth of the plurality of teeth. The first thickness of the shaft between the inner and outer surfaces proximal to the disruptor can be 100-150 microns and the second thickness of the shaft between the inner and outer surfaces distal to the disruptor can be 100-150 microns. The maximum thickness of the tissue disruptor between the inner and the outer surfaces can be about 250-600 microns. The first thickness of the shaft between the inner and outer surfaces proximal to the disruptor can be 100-2000 microns and the second thickness of the shaft between the inner and outer surfaces distal to the disruptor can be 100-550 microns. The maximum thickness of the tissue disruptor between the inner and the outer surfaces can be about 450-600 microns. The tissue disruptor can be a fixed segment of the shaft that dilates and stretches Schlemm's canal prior to or during modification and/or disruption inner or outer walls of Schlemm's canal.

In an interrelated aspect, provided is a method of manufacturing a micro-interventional tool in an assembly-free manner, the micro-interventional tool for use in Schlemm's canal or within an anterior angle of the eye, the method including laser-shaping a flat sheet of super-elastic memory-shape material into a dimension that is between about 5 microns and about 5000 microns.

In an interrelated aspect, provided is a device for disrupting tissue in an eye including a distal portion sized and configured for ab interno insertion into an anterior chamber of the eye for positioning adjacent a trabecular meshwork. The distal portion includes an elongate, flexible shaft comprising a spiral-cut Nitinol tube having a distal end region shaped into a curve and having a radially inner surface and a radially outer surface. A tissue disruptor is coupled to the shaft proximal of the distal-most end on at least one of the inner surface and the outer surface. The tissue disruptor includes a blunt tissue-engaging surface without any cutting element. The shaft is configured to be inserted through the trabecular meshwork and into a portion of Schlemm's Canal so as to be advanced along Schlemm's Canal of the eye away from the portion of Schlemm's Canal. As the shaft advances, the tissue-engaging surface of the protrusion disrupts tissue of the eye.

In an interrelated aspect, provided is a device for disrupting tissue in an eye including a distal portion sized and configured for ab interno insertion into an anterior chamber of the eye for positioning adjacent a trabecular meshwork. The distal portion includes a substantially rigid introducer tube having a proximal end region that extends along a longitudinal axis and a distal end region that curves relative to the longitudinal axis. The distal end region includes a first curved region and a second curved region. The first curved region curves in a first direction at a first radius of curvature and the second curved region curves in a second direction at a second radius of curvature. An elongate, flexible shaft extends at least in part through a lumen of the introducer tube; and a tissue disruptor is coupled to the shaft proximal of the distal-most end on at least one of the inner surface and the outer surface. The tissue disruptor has a blunt tissue-engaging surface without any cutting element. The shaft is configured to be inserted through the trabecular meshwork and into a portion of Schlemm's Canal so as to be advanced along Schlemm's Canal of the eye away from the portion of Schlemm's Canal. As the shaft advances, the tissue-engaging surface of the protrusion disrupts tissue of the eye.

In some variations, one or more of the following can optionally be included in any feasible combination in the above methods, apparatus, devices, and systems. More details are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively, but are intended to be illustrative. Also, relative placement of features and elements may be modified for the purpose of illustrative clarity.

FIG. 1A shows an implementation of a device for removing tissue from an eye having a housing with an actuator to manipulate a tissue engager relative to an introducer tube having a minimal curvature;

FIG. 1B is a detail view of a distal end region of the device of FIG. 1A;

FIG. 1C is a detail view of the tissue engager shown in FIG. 1B taken at circle C;

FIG. 5A is a side view of an implementation of a shaft having a tissue engager for use with any of the devices described herein;

FIG. 5B is a detailed view of the tissue engager of FIG. 5A;

FIG. 6A is a side view of a device shaft having an implementation of a tissue engager shown in the retracted configuration;

FIG. 6B is a side view of the device of FIG. 6A with the tissue engager shown in the extended configuration;

FIG. 11 shows in schematic a device introduced into the entry opening and advanced towards the terminal opening;

FIG. 12A is a perspective view of an implementation of an introducer tube having a dual curve and for use with any of the devices described herein;

FIG. 12B is a side view of the introducer tube of FIG. 12A;

FIG. 12C is a cross-sectional view of the introducer tube of FIG. 12B taken along line A-A;

FIG. 12D is a detailed view of FIG. 12C taken along circle B;

FIG. 14A is a side view of an implementation of an introducer tube having a dual curve for use with any of the devices described herein with the shaft extended;

FIG. 14B is a side view of the introducer tube of FIG. 14A with the shaft retracted;

FIG. 14C is a perspective view of the introducer tube of FIG. 14A with the shaft extended;

FIG. 14D is a perspective view of the introducer tube of FIG. 14B with the shaft retracted;

FIG. 14E is a detailed view of the distal end region of the shaft of FIG. 14D;

FIG. 14F is a side view of an implementation of a shaft having a tissue engager for use with any of the devices described herein;

FIG. 14G is a detailed view of the tissue engager of FIG. 14F;

FIG. 16C is a perspective view of the introducer tube of FIG. 16A with the shaft extended;

FIG. 16D is a perspective view of the introducer tube of FIG. 16B with the shaft retracted;

FIG. 16E is a detailed view of the distal end region of the shaft of FIG. 16D;

FIGS. 17A-17B illustrate various curvatures of the dual curve introducer tube for use with any of the devices described herein;

FIG. 18A is a side view of an implementation of a shaft having a tissue disruptor for use with any of the devices described herein;

FIG. 18B is a detailed view of the shaft of FIG. 18A taken along circle A;

FIG. 18C is a detailed view of the shaft of FIG. 18B taken along circle B;

FIG. 19A is a perspective view of an implementation of a shaft having a tissue disruptor for use with any of the devices described herein;

FIGS. 19B-19C are detailed view of the distal end region of the shaft of FIG. 19A;

FIG. 20A is a side view of the distal end region of the shaft of FIG. 19A;

FIG. 20B is a side view of a distal end region of a shaft having a tissue disruptor for use with any of the devices described herein;

FIG. 20C is a side view of a distal end region of a shaft having a tissue disruptor for use with any of the devices described herein;

Figure 2A:
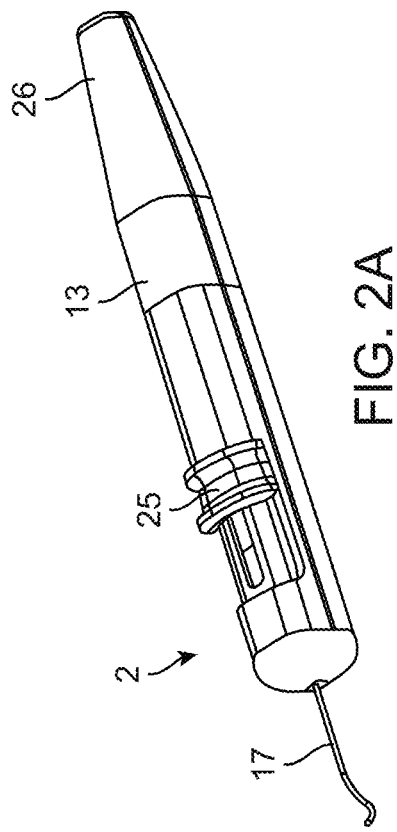
FIG. 2A shows a device for removing tissue from an eye having a housing with an actuator to manipulate a tissue engager and having an introducer tube with a dual curve.
Figure 2B:
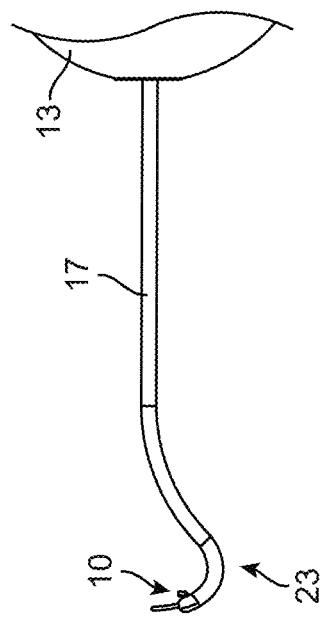
FIG. 2B is a detail view of a distal end region of the device of FIG. 2A.
Figure 2C:
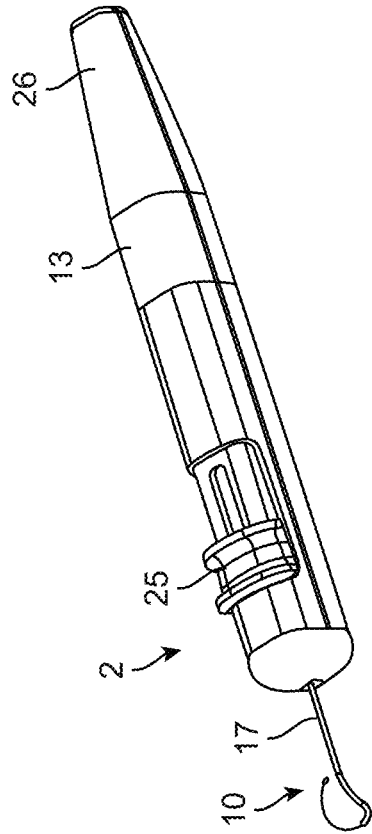
FIG. 2C shows the device of FIG. 2A with the tissue engager in an extended configuration.
Figure 2D:
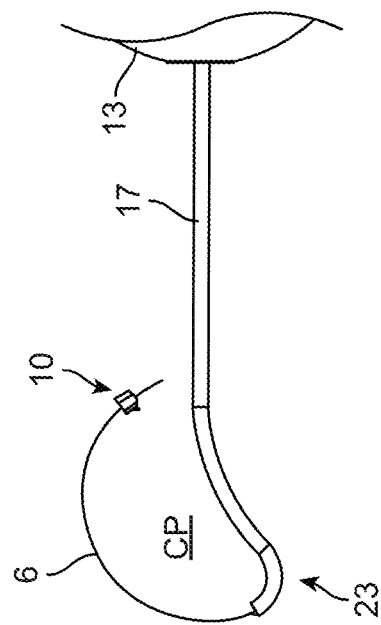
FIG. 2D is a detail view of a distal end region of the device of FIG. 2C.

It should be appreciated that the drawings herein are for illustration only and are not meant to be to scale.

DETAILED DESCRIPTION

The present disclosure relates generally to the field of ophthalmics, more particularly to increasing aqueous drainage of the eye. In one specific application, for example, the devices and methods may be used to remove trabecular meshwork (with or without part of Schlemm's canal) to treat glaucoma and other conditions. The devices described herein can disrupt the inner wall of Schlemm's Canal (i.e., the trabeculorhexis) without cutting, for example, by bluntly engaging, tearing, and/or shearing or otherwise modifying the trabecular tissue, such as by a disinsertion of the trabecular meshwork from its attachment to the sclera and surrounding gonio anatomy, which will be described in more detail below. The devices described herein may simultaneously disrupt tissue of the inner canal wall and modify the outer canal wall (i.e., the sclera). For example, a distal portion of the device inserted into the anterior chamber of the eye can have a first protrusion extending radially inwardly and a second protrusion disposed radially outwardly. Positioning the distal portion adjacent the trabecular meshwork and advancing it along a circumferential contour of Schlemm's Canal can disrupt the trabecular meshwork with the first protrusion as the device is advanced and, at the same time, disrupt the outer wall of Schlemm's Canal with the second protrusion. The first protrusion can remove a portion of an inner wall of Schlemm's Canal by bluntly tearing or disinserting the trabecular meshwork tissue, without cutting while the second protrusion can cut, slit, abrade, shave, debride, micro-perforate, and/or otherwise modify or disrupt the outer wall. In still further implementations, the devices described herein can be used to disrupt the inner wall prior to modification of the outer wall. In this implementation, no enclosed canal is present in the anterior angle along at least a portion of the circumference of the eye prior to the modification of the outer wall because the inner wall formed by the trabecular meshwork has already been disrupted. The modification of the outer wall also need not be limited to the outer wall of what would otherwise be Schlemm's Canal as the devices can be used to modify the scleral wall from above the supraciliary segment at a posterior limit to below the clear-corneal margin/limbus at an anterior limit. A relatively wide band of the eye can be modified with the tools described here. The modification to the outer wall that can be performed after or prior to excisional or incisional removal, ablation, or disruption of the trabecular meshwork can vary (e.g., thinning, cutting, abrading, microporation, stenting, and other tissue modifications known in ophthalmology). The modifications and methods using the devices described herein will be described in more detail below. In some implementations the tissue disruptor for the outer wall can incorporate microserrations for outer wall thinning and canaloplasty to improve canalicular/trans-scleral outflow as will be described in more detail below. In some implementations, the tissue disruptor can be positioned on an outer dimension of the tool and yet disrupts the inner wall without impacting the outer wall due to a wedging effect as will be described in more detail below. The outer wall modification can also include disruption using RF ablation or other electro or heat ablation process through the architecture of the outer-facing surface of a disruptor. The outer canal wall includes selectively and/or collectively any of the anatomic structures that are positioned radially outward from the canal including the endothelial layer of the Schlemm's canal as well as the adjacent scleral tissue.

FIGS. 1A-1C and also FIGS. 2A-2D illustrate an implementation of a device 2 for disrupting tissue within the anterior angle of the eye having a distal tissue engager 10 mounted to a flexible shaft 6. The device 2 can include a proximal housing 13 or hand piece having an introducer tube 17 projecting from a distal end region of the housing 13. The shaft 6 extends through the introducer tube 17 and can project relative to the introducer tube 17 and the housing 13 along a variety of lengths using one or more actuators 25 on the housing 13. Each of the device components will be described in more detail below.

Figure 13C:
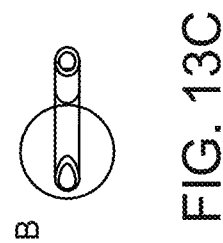
FIG. 13C is a cross-sectional view of the introducer tube of FIG. 13B taken along line A-A.
Figure 13D:
FIG. 13D is a detailed view of FIG. 13C taken along circle B.
Figure 13A:
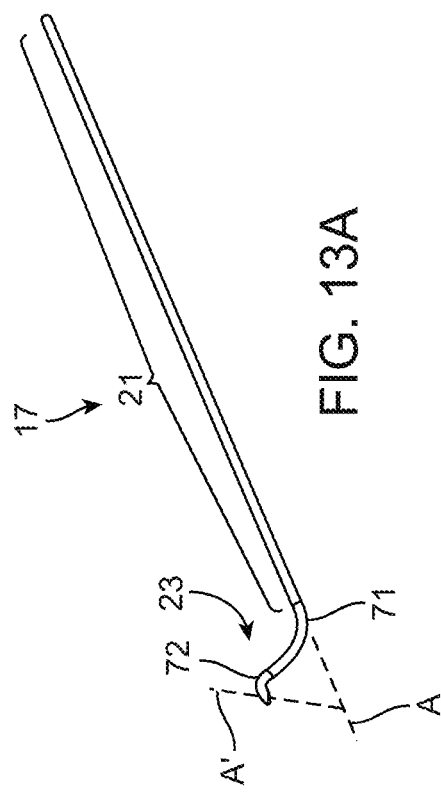
FIG. 13A is a perspective view of an implementation of an introducer tube having a dual curve and for use with any of the devices described herein.
Figure 13B:
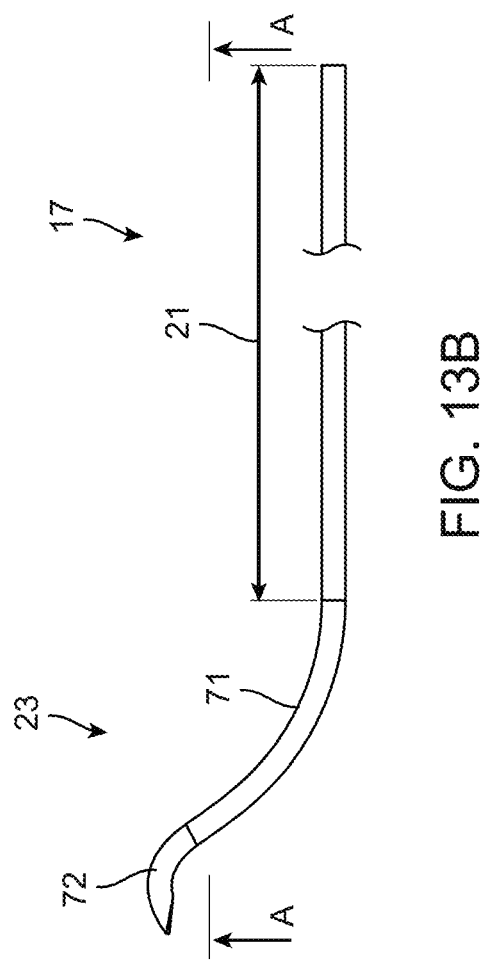
FIG. 13B is a side view of the introducer tube of FIG. 13A.

The introducer tube 17 coupled to and extending distal from the housing 13 can be a tubular element having a lumen 19 extending through it such that the elongate shaft 6 extends through the lumen 19 of the introducer tube 17 (see FIGS. 2B, 2D, 3C-3D, 4C-4D, 12A-12D, 13A-13D, 14A-14D, 15, 16A-16D, and 17A-17B). The introducer tube 17 can be a stainless steel tube, for example, a 0.022" tube or between 0.020" and 0.028" or having a size configured to insert through a clear corneal incision less than about 2.75 mm, or less than 2.5 mm, or about 1 mm. The distal-most end of the introducer tube 17 can be designed to facilitate engagement into the canal, but is preferably not sharp. The distal edge 27 surrounding the distal opening 29 from the lumen 19 are preferably rounded without any sharp edges. The shape of the distal opening 29 can be circular or non-circular. In some implementations, the distal opening 29 is formed at a distal end of the introducer tube 17 at an oblique angle such that the shape of the distal opening 29 is slightly elongate, elliptical, oval, or egg-shaped (see FIG. 13D).

The introducer tube 17 of the devices described herein can be substantially straight and extend along a longitudinal axis A from its proximal end to its distal end. The introducer tube 17 can also be curved or incorporate a curve along at least a portion of its length (see FIGS. 1B, 2B, 2D, 3A-3B, 4A-4B, 12A-12D, 13A-13D, 14A-14D, 15, 16A-16D, and 17A-17B). The introducer tube 17 may have a curved distal end region 23 to facilitate insertion of the device 2 into the trabecular meshwork and to direct the tissue engager 10 of the shaft 6 in the desired direction along the anterior angle. The introducer tube 17 can have a curve that is at least 3 mm radial curvature up to about 10 mm radial curvature for tangential deployment of the shaft 6. The radial curvature of the introducer tube 17 preferably does not exceed 10 mm radius.

In some implementations, the curve of the introducer tube 17 can be a dual curve and resemble a "shepherd's crook" and provide the user with a surface to press into the anterior angle against the inner wall of Schlemm's Canal, which can then allow easier alignment and deployment of the shaft to disrupt the eye tissues. FIGS. 2A, 3A, 4A, 6A, 7A, 12A, 13A and others show implementations of the introducer tube 17 having a proximal end region 21 that extends away from the housing 13 in a substantially straight manner along a longitudinal axis A and the distal end region 23 of the introducer tube 17 curves relative to the longitudinal axis A. The distal end region 23 of the introducer tube 17 can have a first curved region 71 and a second curved region 72. The first curved region 71 can curve in a first direction at a first radius of curvature and the second curved region 72 can curve in a second direction at a second radius of curvature. The curvature provides better positioning of the tissue engager 10, which will be described in more detail below. Generally, the curves 71, 72 of the introducer tube 17 can work together to bring the tip of the tube 17 to a 1 o'clock or a 2 o'clock position (assuming the surgeon inserts the introducer tube 17 from the 6 o'clock position) for advancement of the shaft 6 from the tube 17 to disrupt eye tissue. The curves can combine to bring the tip of the tube so it is nearly tangential with the curvature of Schlemm's Canal. FIGS. 17A-17B illustrate various curvatures of the introducer tube 17 considered herein that are configured to direct the distal end region 23 in a particular relationship to the proximal end 21.

Figure 3A:
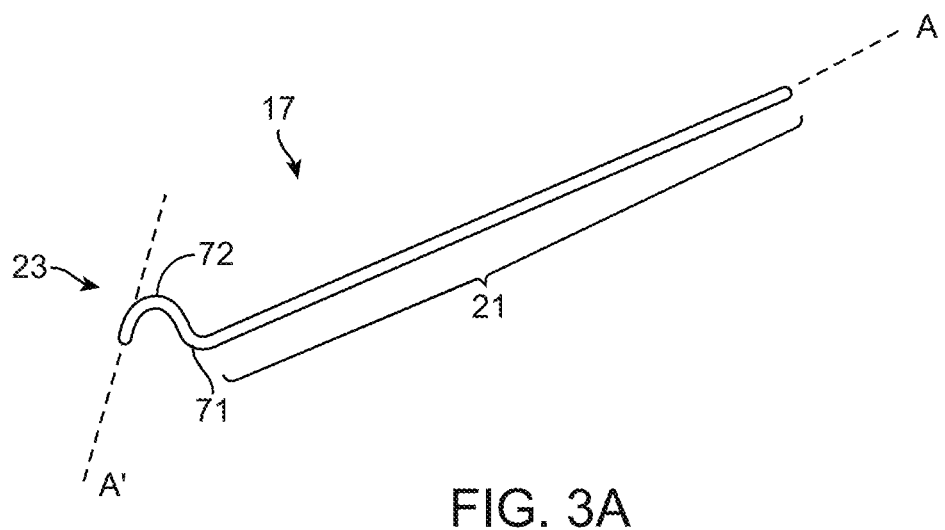
FIG. 3A is a perspective view of an implementation of an introducer tube having a dual curve and for use with any of the devices described herein.
Figure 3B:
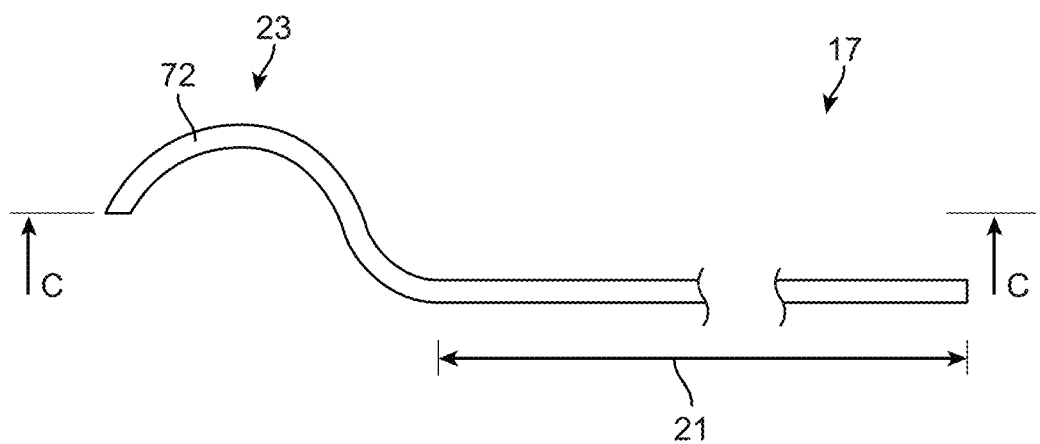
FIG. 3B is a side view of the introducer tube of FIG. 3A.
Figure 3C:
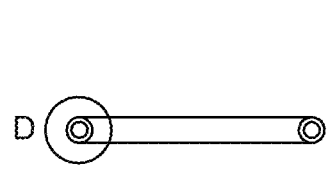
FIG. 3C is a cross-sectional view of the introducer tube of FIG. 3B taken along line C-C.
Figure 3D:
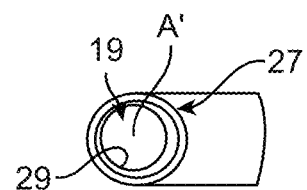
FIG. 3D is a detailed view of FIG. 3C taken along circle D.
Figure 4A:
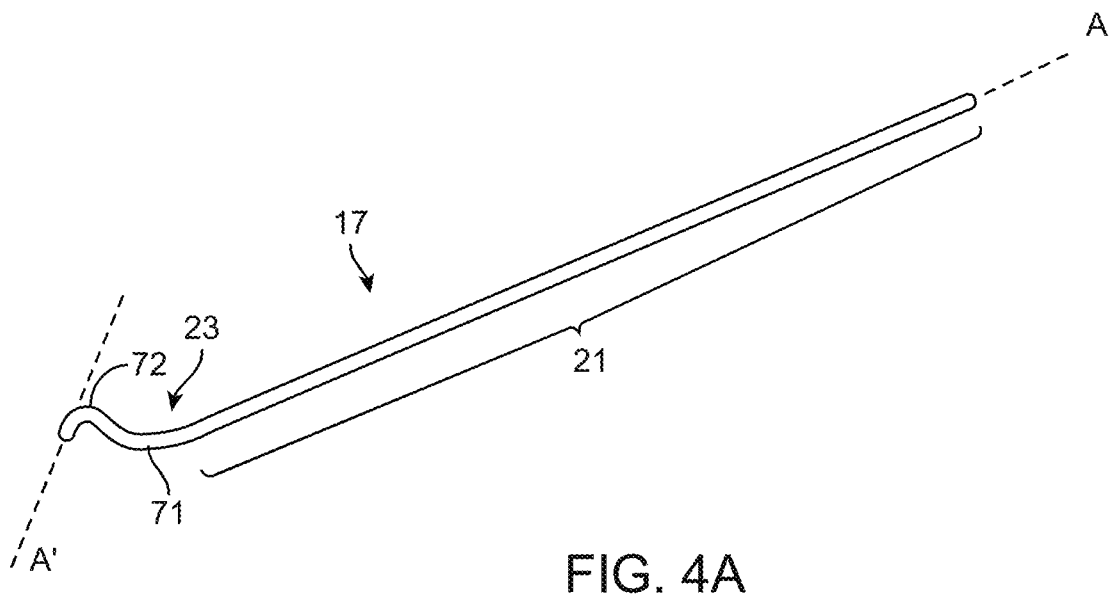
FIG. 4A is a perspective view of an implementation of an introducer tube having a dual curve and for use with any of the devices described herein.
Figure 4B:
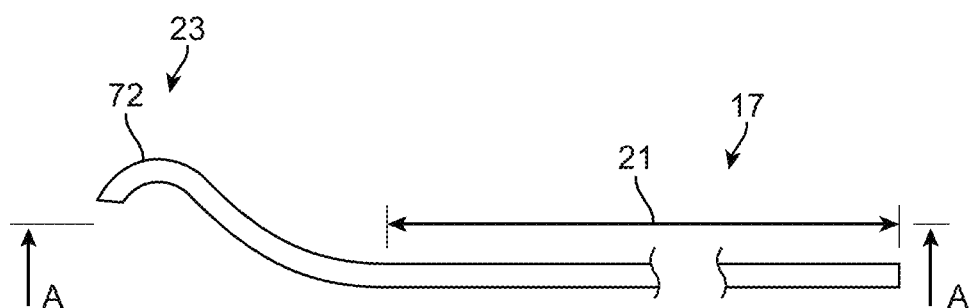
FIG. 4B is a side view of the introducer tube of FIG. 4A.
Figure 4C:
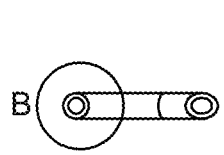
FIG. 4C is a cross-sectional view of the introducer tube of FIG. 4B taken along line A-A.
Figure 4D:
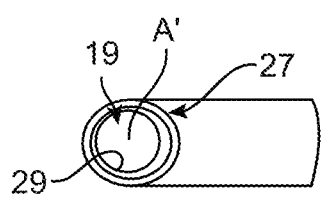
FIG. 4D is a detailed view of FIG. 4C taken along circle B.

In the implementation shown in FIGS. 3A-3B, the first curved region 71 can have a radius of curvature that is about 2.1 mm and the second curved region 72 can have a radius of curvature of about 3.2 mm. FIGS. 4A and 4B show another implementation having a larger radius of curvature in the first curved region 71 (e.g., about 8.6 mm) and a smaller radius of curvature in the second curved region 72 (e.g., about 1.3 mm). The first curved region 71 can have a larger radius of curvature that is between 2.0 mm and 9.0 mm and the second curved region 72 can have a smaller radius of curvature that is between 1.0 mm and 4.0 mm. In some implementations, the second curved region 72 of the tube 17 can substantially match the radius of curvature of the eye. The first curved region 71 can extend along a length of about 2.0 mm up to about 6.1 mm. In some implementations, the curve of the distal end region 23 of the introducer tube 17 may be about 15-60 degrees.

The proximal end region 21 of the introducer tube 17 extending along the longitudinal axis A can project outside the housing 13 about 50 mm up to about 75 mm. The distal end region 23 of the introducer tube 17 can provide about 5 mm-15 mm extended reach beyond a length the proximal end region 21. Thus, the introducer tube 17 can have approximately 55 mm to about 85 mm total length beyond a distal end of the housing 13. The length of the proximal end region 21, which can be at least 10 mm to 14 mm away from the distal tip 27 of the tube 17, allows for the distal end region 23 to access the target site within the anterior angle while the substantially straight proximal end region 21 is maintained at the corneal incision site. Meaning, the portion of the tube 17 extending through the corneal incision site during use is the substantially straight proximal portion 21. This allows the user to rotate the tube 17 clockwise or counter-clockwise during use without inadvertently torqueing the incisional area.

In both implementations, the curvature of the distal end region 23 of the introducer tube 17 can result in the distal opening 29 from the lumen 19 to surround an axis A' that is at an angle to the longitudinal axis A of the proximal end region 21 of the introducer tube 17. In some implementations, the angle of axis A' relative to the longitudinal axis A is approximately 45, 50, 55, 60, 65, 70, 75, 80, 85, 90, 95, 100, or about 105 degrees or anywhere there between. Further, the distal opening 29 can be off-set a distance from the longitudinal axis A of the proximal end region 21 of the tube 17, such as between about 2 mm up to about 5 mm.

FIGS. 14A-14D illustrates another implementation of the introducer tube 17 having two curvatures. FIG. 14A shows the shaft 6 extended out from the introducer tube 17 and FIG. 14B shows the shaft 6 retracted within the introducer tube so that the tissue disruptor 75 is substantially contained within the lumen of the tube 17. FIGS. 14C-14D are the same as FIGS. 14A-14B rotated slightly to illustrate the distal opening 29 from the lumen 19. FIG. 14E is a detailed view of the shaft 6 of the device in FIGS. 14A and 14C illustrating the tissue disruptor 75 positioned near a distal end region of the shaft 6. FIG. 14F-14G are additional view of a shaft 6 having a triangular-shaped issue disruptor 75 positioned near a distal end region of the shaft 6 on the inner curvature. The introducer tube 17 of FIGS. 14A-14D can be used with a tissue disruptor on a shaft having any of a variety of configurations described herein and as shown in FIGS. 1A-1C, 2A-2D, 5A-5B, 6A-6C, 7A-7B, 8A-8D, 9A-9D, 14A-14G, 15, 16A-16E, 18A-18C, 19A-19C, and 20A-20F. The forward-facing surface of the disruptor 75 on the inner curvature can form an angle with the inner-facing surface of the shaft 6 that is greater than 90 degrees. The proximal-facing surface of the disruptor 75 on the inner curvature can form an angle with the inner-facing surface of the shaft 6 that is greater than, less than, or equal to 90 degrees. FIG. 14G illustrates an angle between the forward-facing surface of the disruptor 75 and the inner-facing surface of the shaft 6 that is about 135 degrees and an angle between the proximal-facing surface of the disruptor 75 and the inner-facing surface of the shaft 6 that is about 90 degrees.

Disrupting Schlemm's canal (e.g. with a first tool, such as the radially inward projecting disruptor 75) eliminates the presence of the canal entirely so that modifications to the outer wall can be performed more easily and without size restrictions that would otherwise be present if the canal were preserved. The tools and methods described herein allow for accessing the outer wall in a non-cannulated ab interno manner so that the outer wall can be modified. The non-cannulated ab interno manner of outer wall modification allows for the outer wall tool size to be increased or at least unfettered by the size limitations posed by Schlemm's canal. Generally, inserting a tool within Schlemm's canal while preserving the canal requires a maximum outer diameter of up to about 500-550 microns. The tool size useful for modifying the outer wall in the absence of the trabecular meshwork without an intact Schlemm's canal can be relatively larger than 150 microns, for example, up to about 2 mm. The larger tool size provides the bulk and heft useful for cutting, abrading, shaving, thinning, perforating, or otherwise modifying the tougher scleral tissue forming the outer wall of Schlemm's. Even with the larger tool size, the actual outer wall modification can be minimal (less than about 150 micron sized cuts). Where the tools are described herein as having a tissue disruptor directed radially inward from the shaft, the tool can additionally incorporate a tissue disruptor or cutter projecting radially outward so that the inner wall modification to the trabecular meshwork can be performed simultaneously with the outer wall modification to the scleral tissue. The tools described herein can alternatively incorporate a tissue disruptor or cutter projecting radially outward from the shaft so that the outer wall modification can be performed separately from the inner wall modification. The inner wall modification can be performed as a first step and the outer wall modification can be performed as a second step. Where a feature projects radially inward from the shaft 6, the feature can be blunt or sharpened to disrupt the trabecular meshwork, which is a relative thin and delicate tissue type that is relatively easily disinserted. Where a feature projects radially outward from the shaft 6, the feature can be sharpened, serrated, and/or abrasive to cut, debride, reduce, thin, and/or shave the tougher scleral tissue forming the outer wall of Schlemm's canal. Where a single tissue disruptor or cutter is described as projecting radially inward or radially outward, more than a single tissue disruptor or cutter can be incorporated so that the plurality of tissue disruptors/cutters can create a micro-serration to the shaft 6 on either a radially inner surface of the shaft 6, a radially outer surface of the shaft 6, or both radially inner and radially outer surfaces of the shaft 6.

The shaft 6 can, but need not be a guidewire. In some implementations, the shaft 6 is formed from a flat sheet of material that is shaped by cutting and/or micro-machining into an elongate element forming the tissue engager 10 of the shaft 6 (www.memry.com/laser-cutting). The sheet may be cut by a laser to the desired geometry and/or shape. The starting material may be sheet of Nitinol that is between about 75 microns and 550 microns thick or more preferably between about 100 microns and about 150 microns thick. A shaft 6 cut, shaped, or printed from the flat sheet need not have a round cross section although the sheet can be curled into a round cross-section, if desired. The sheet of material can be cut into an elongate shape having an inner and outer curved surfaces. In some implementations, the tissue engager 10 is one or more disruptors 75 on an inner curved surface of the shaft 6. In other implementations, the tissue engager 10 is one or more disruptors 75 on an outer curved surface of the shaft 6. In still further implementations, the tissue engager 10 is one or more disruptors 75 on both the inner and outer curved surfaces of the shaft 6. The manufacturing process of the micro-interventional instrumentation components for use in the canal or within the anterior angle of the eye can include laser-printing and/or laser-shaping a flat sheet of super-elastic memory-shape material to dimensions that are as small as 5 microns up to about 5,000 microns. The manufacturing process needs no micromachining and/or molding of the components. The manufacturing process provides cost-effective automated or semi-automated manufacturing of gonio-disruptors, gonio-shafts, and/or gonio-probes in an assembly-free manner.

FIGS. 18A-18C illustrate an implementation of a shaft 6 formed from a Nitinol flat sheet having a thickness of about 100 microns to about 150 microns. The shaft 6 can be used with any of the devices described herein and extend through a lumen 19 of an introducer tube 17 projecting from a distal end region of the housing 13 where the tube 17 is straight and extends along a long axis from its proximal end to its distal end or is at least partially curved along its length including a dual curve as discussed above. The shaft 6 of FIGS. 18A-18C can be used with an introducer tube 17 having any of a variety of configurations described herein and as shown in FIGS. 1A-1C, 2A-2D, 3A-3D, 4A-4D, 6A-6C, 7A-7B, 12A-12D, 13A-13D, 14A-14D, 15, 16A-16D, and 17A-17B.

Again with respect to FIGS. 18A-18C, the sheet (having a thickness of about 100-150 microns, for example, or as large as 2000 microns) may be cut to a width of about 0.010 cm to about 0.015 cm and having a total length about 150 cm up to about 170 cm, the curved portion being about 20 mm of the total length. The sheet may be laser-shaped into the elongate, flexible shaft having a non-circular cross-section and a distal end region comprising any of a variety of tissue disrupting profiles, which will be described in more detail below. A distal end region of the shaft 6 may be shaped into a curve forming a curved portion 11 having a central plane CP as described elsewhere herein (e.g., about 220 degrees-230 degrees). FIG. 18B shows a detail view of the curved portion 11 of the distal end region of the shaft 6 having a tissue engager 10. The distal end region of the shaft 6 has a radially inner surface 7 connected to a radially outer surface 8 by two lateral sides 9. FIG. 18C shows the distal-most end 73 of the shaft 6, which can have rounded distal-facing edges formed to have a smooth ball tip that is blunt for circumferential gonio-traction. The rounded edges on the distal face of the shaft 6 allow for the shaft to slide better relative to the tissue compared to square edges. The lateral edges, in contrast, can be rounded or square cut. A disruptor 75 is formed on the inner surface of the curved portion 11 of the shaft 6. The distal face 76 of the disruptor 75 may slope gently from the thickness of the shaft 6, the thickness being between the inner and outer surfaces of the shaft distal to the disruptor 75, to the maximum thickness of the disruptor 75, the maximum thickness being between the inner and outer surfaces of the shaft. The proximal face 77 of the disruptor 75 can taper down to the thickness of the shaft 6, the thickness being between the inner and outer surfaces of the shaft proximal to the disruptor 75. The distal face 76 of the disruptor is a blunt tissue-engaging surface without any cutting element. A short segment forming a distal guide member 15 can extend distal to the location of the disruptor 75. The length of the distal guide member 15 can vary, such as from about 1 mm up to about 5 mm. Thus, the smooth ball tip of the shaft can be located 1 mm-5 mm away from the distal face of the disruptor.

The thickness of the shaft between the inner and outer surfaces distal to the disruptor can be about 100-150 microns. The thickness of the shaft between the inner and outer surfaces proximal to the disruptor can also be about 100-150 microns. The thickness of the shaft proximal to the disruptor can be larger (e.g., as large as up to about 2000 microns) because once the disruptor has opened up the canal, the proximal shaft dimensions are no longer limited by the size of the canal, but by the size of the corneal incision. The thickness of the shaft distal to the disruptor can also be larger than about 150 microns, such as up to about 450 microns. The maximum thickness of the tissue disruptor between the inner and outer surfaces can be about 250-325 microns or 250-600 microns (e.g., about 450-600 microns, preferably at least about 550 microns). The tissue disruptor can be a fixed dilatory segment of the shaft configured to dilate and stretch Schlemm's canal prior to and during modification and/or disruption of the inner and/or outer walls of Schlemm's canal. Stretching of the canal wall may further improve outflow as it may expand the canaliculi and ostia.

The elongate, flexible shaft of superelastic material is sized and configured for ab interno insertion into the anterior chamber of the eye. The distal end region of the shaft is shaped into a curve having a central plane. The cross-sectional shape of the shaft, if taken transverse to the length of the shaft between a distal end and a proximal end, can be generally non-circular, such as square or rectangular. As mentioned above, the distal end region of the shaft has a radially inner surface 7 connected to a radially outer surface 8 by two lateral sides 9. The inner surface 7 and outer surface 8 of the shaft 6 along the curved portion can be curved whereas the two lateral sides 9 can be planar or straight. The tissue engager 10 embodiment of the shaft 6 shown in FIGS. 18A-18C has a single inwardly projecting tissue disruptor 75 on the radially inner surface 7 of the shaft. FIGS. 19A-19C illustrate another implementation of a tissue engager 10 on the shaft 6 having an inwardly projecting disruptor 75a on the radially inner surface 7 of the distal end region of the shaft and an outwardly projecting toothed disruptor 75b on the radially outer surface 8 opposite the inwardly projecting disruptor. The disruptors on the inner and outer surfaces can be opposite one another along the length of the shaft or on opposite sides by off-set longitudinally along the length of the shaft. For example, the outer wall disrupting feature may be further proximal than the inner wall disrupting feature located further distal along the shaft so that the inner wall and outer wall disrupting features are on opposite sides, but not perfectly opposite one another and merely near one another. As with other implementations, the shaft 6 can be formed from a Nitinol flat sheet having a thickness of about 100 microns to about 500 microns cut to a desired specification. The flat sheet can be cut into an elongate, flexible shaft (e.g., 150-170 cm) having a non-circular cross-section and a distal end region having a particular tissue disrupting profile. A proximal end region of the shaft can be cut to have a width of about 0.010 cm to about 0.015 cm. A distal end region of the shaft can be cut to have a tissue disruptor profile that widens relative to the proximal end region of the shaft. The tissue disrupting profile can vary and can include a tissue disruptor 75 located proximal of a distal-most end 73 of the shaft 6 on at least one of the inner surface 7 and the outer surface 8. As discussed elsewhere herein, the tissue disruptor 75 can include a distal face, a proximal face, and a maximum thickness between the inner and outer surfaces. The distal face may slope from a first thickness of the shaft 6 distal to the tissue disruptor 75 towards the maximum thickness. The proximal face may taper down from the maximum thickness to a second thickness of the shaft 6 proximal to the tissue disruptor 75. The thickness of the shaft 6 between the lateral sides 9 is a function of the thickness of the flat sheet stock material. Although the sheet stock material thickness can vary as is available in the art, preferably a 100 micron thick Nitinol sheet or a 150 micron thick Nitinol sheet is desired. The thicknesses (and overall shape profile) of the shaft 6 between the inner and outer surfaces, however, can vary and is controlled by the programmed cut profile. Different cut profiles may be selected based on the intended anatomy of the tool and the type of tissue disruption desired. The maximum thickness of the tissue disruptor 75 can vary, but is preferably about 250-325 microns when measured between the inner and outer surfaces compared to the thickness of the shaft proximal and distal to the tissue disruptor, which is preferably about 100-150 microns. The thickness of the shaft between the inner and outer surfaces proximal to the disruptor can be larger than this up to about 2000 microns whereas the thickness of the shaft between the inner and outer surfaces distal to the disruptor can be 100-450 microns The tissue disrupting profile at the distal end region of the shaft 6 may include two tissue disruptors— one formed on the inner surface 7 and one formed on the outer surface 8 opposite the first tissue disruptor or even at a different location along a length of the shaft 6. The manufacturing methods of laser-shaping a flat sheet of super-elastic memory-shape material into a dimension (e.g., between 5-5000 microns) allows for an assembly-free manner of creating micro-interventional tools for use in Schlemm's canal or near an anterior angle of the eye.

Again with respect to FIGS. 19A-19C, the distal end region of the shaft 6 may be shaped to have a curved portion 11 having a central plane CP as described elsewhere herein. The distal-most end 73 of the shaft 6 may be blunt or formed (such as by laser-cutting) into a smooth ball tip 73. The edges on the distal face of the shaft 6 forming the distal-most end 73 are preferable rounded to allow for the shaft to slide better relative to the tissue compared to square edges. The lateral edges (i.e. edges formed where the inner surface 7 meets the lateral sides 9 and the outer surface 8 meet the lateral sides 9) can be rounded or square-cut. The disruptor 75a, proximal of the distal-most end 73, formed on the inner surface may slope gently from the thickness of the shaft 6 distal to the disruptor 75a to a thickness of the disruptor 75a. The proximal face 77a of the inwardly facing disruptor 75a can taper down from the thickness of the disruptor 75a to a thickness of the shaft 6 proximal to the disruptor 75a. A distal guide member 15 can extend distal to the location of the disruptor 75a. The length of the distal guide member 15 can vary, such as from about 1 mm and 5 mm, preferably between about 1 mm and 3 mm, about 1.5 mm to about 2 mm, or less than 3 mm down to about 1 mm.

The shaft 6 can be used with any of the devices described herein and extend through a lumen 19 of an introducer tube 17 projecting from a distal end region of the housing 13 where the tube 17 is straight and extends along a long axis from its proximal end to its distal end or is at least partially curved along its length including a dual curve as discussed above. The shaft 6 of FIGS. 19A-19C can be used with an introducer tube 17 having any of a variety of configurations described herein and as shown in FIGS. 1A-1C, 2A-2D, 3A-3D, 4A-4D, 6A-6C, 7A-7B, 12A-12D, 13A-13D, 14A-14D, 15, 16A-16D, and 17A-17B.

Figure 20D:
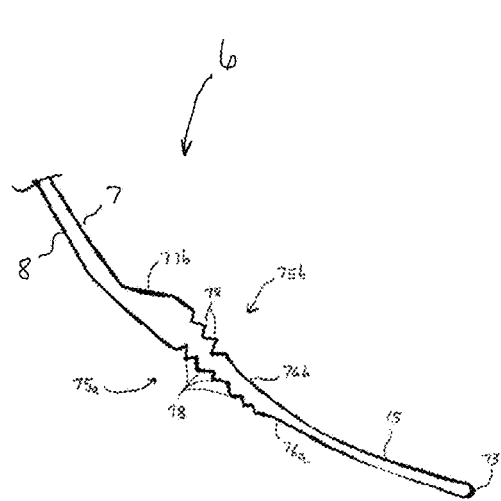
FIGS. 20D-20F are side views of a distal end region of a shaft having a tissue disruptor for use with any of the devices described herein.

As mentioned, the tissue engager 10 of the shaft 6 can have an additional disruptor 75b projecting from the outer surface 8. Still with regard to FIGS. 19A-19C and also FIGS. 20A-20F, the disruptor 75b formed on the outer surface 8 of the shaft 6 can incorporate a plurality of teeth 78. The distal guide member 15 extending distal to the disruptor 75b may slope gently towards the first tooth 78 of the disruptor 75b. A distal face 76b of the disruptor 75b slopes from the thickness of the guide member 15 (e.g., about 100-150 microns) up to a thickness of the first tooth 78 (e.g., about 250 microns). The teeth 78 of the disruptor 75b can be separated from one another by a gap 79. The gap 79 may vary in size so that the teeth 78 are spaced from one another by about 200 microns up to about 350 microns. The gap 79 of the embodiment of FIG. 20A is about 100 microns whereas the gap 79 of the embodiment in FIG. 20B is about 210 microns resulting in narrower teeth 78 compared to the embodiment of FIG. 20A. Each tooth 78 can have the same height (see FIG. 20A) or one or more of the plurality of teeth 78 may vary in height (see FIG. 20B). In the implementation shown in FIG. 20B, a first tooth 78a projects outward a first height so that its thickness (i.e., the thickness from inner surface to outer surface of the shaft at that location) is about 250 microns, a second tooth 78b projects outward a second height so that its thickness is about 275 microns, a third tooth 78c projects outward a third height so that its thickness is about 300 microns, and a fourth tooth 78d projects outward a fourth height so that its thickness is the maximum thickness of the disruptor 75b (e.g., 325 microns). The plurality of teeth 78 of the disruptor 75b need not vary in the height they project outward and can be more uniform or alternating in heights. Any of a variety of combinations is considered herein. The geometry of each tooth 78 can be generally square-cut although other geometries are considered.

Figure 20E:
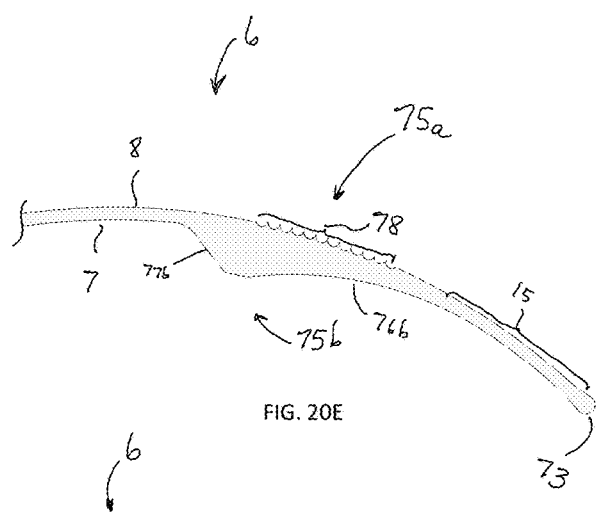
Figure 20F:
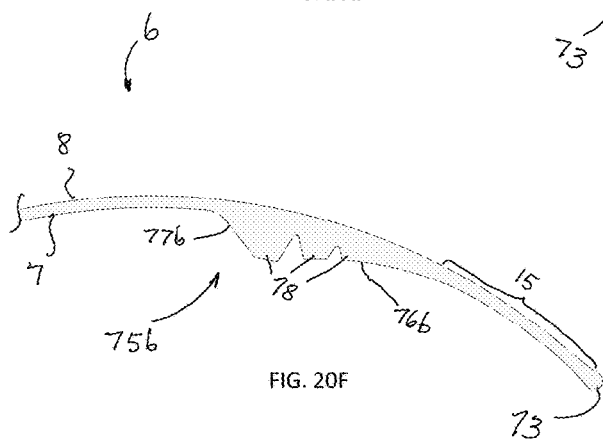

The geometry of each tooth 78 may be more triangular forming a plurality of shearing serrations (see FIGS. 20D-20E). The serrations 78 of the disruptor 75 shown in FIG. 20D are positioned on both the inner surface 7 and the outer surface 8 of the shaft 6 whereas the serrations 78 of the disruptor 75 shown in FIG. 20E are only on the outer surface 8. FIG. 20F shows a single-sided disruptor 75 having a combination of square-cut and triangular cut teeth 78. The teeth 78 in the disruptor 75 of FIG. 20F are only on the inner surface 7. Any of a variety of geometries is considered herein on both the inner and outer surfaces 7, 8 or on just the inner surface 7 or just the outer surface 8 of the shaft 6. The maximum thickness of the disruptor 75, regardless the shape or configuration of the teeth or serrations, can be between 550-600 microns to ensure the tissue is disrupted rather than merely stretched.

FIG. 20A shows a distal end region of a shaft 6 with a disruptor 75a on the inner surface 7 as well as the toothed disruptor 75b on the outer surface 8. FIG. 20B shows a distal end region of a shaft 6 with a disruptor 75b on only the outer surface 8. The presence of the two disruptors on the embodiment of FIG. 20A creates an initial ramp height that is about 330 microns thick compared to the initial ramp height of FIG. 20B that is only about 250 microns thick.

In some implementations, the disruptor 75 of the shaft 6 can project radially outward from the outer surface 8 of the shaft 6 and yet disrupt tissues positioned radially inward relative to the shaft 6. FIG. 20C illustrates an implementation of a tissue engager 10 of the shaft 6 having a disruptor 75 projecting radially outward from the outer surface 8 of the shaft 6 and the inner surface 7 being relatively uniform or smooth with the curve proximal and distal to the location of the disruptor 75. The outwardly projecting disruptor 75 of FIG. 20C may disrupt tissues radially inward relative to the shaft 6 (i.e., the trabecular meshwork) during advancement due to the disruptor 75 abutting against the outer wall and being sized and shaped to urge the shaft 6 radially inward so that the inner curvature of the shaft 6, which may be uniform and smooth without any disruptor per se, drags along the trabecular meshwork thereby disrupting it. The shape of the outer curvature disruptor 75 can be designed to slide along the outer wall so as to direct the distal tip 73 of the shaft inward back out of the canal so as to disrupt the trabecular meshwork during advancement of the shaft 6 in the advancement direction.

The shearing serrations or teeth 78 positioned on a wedge-shaped disruptor 75 can include a canal-probing dilating ball-tipped distal end 73 extending distal to the disruptor 75. The ball-tipped distal end 73 can allow guided traction within the canal during forward disruption. As discussed elsewhere herein, the cross-sectional shape of the shaft 6, if taken transverse to the length of the shaft 6 between a distal end and a proximal end, can be generally non-circular, such as square or rectangular. The shaft 6 if not cut into a ball-shape or other atraumatic shape would be problematic during advancement through the canal because the leading square edges would tend to snag or cut tissue. The forward-facing edges of the shaft 6 at the distal end 73 are cut so as to be rounded to avoid this.

The length of the guide member 15 separating the ball tip 73 from the wedge disruptor 75 can vary, but may be between 1 mm and 5 mm, preferably between about 1 mm and 3 mm, about 1.5 mm to about 2 mm, or less than 3 mm down to about 1 mm.

The shaft 6 of FIGS. 20A-20F can be used with any of the devices described herein and extend through a lumen 19 of an introducer tube 17 projecting from a distal end region of the housing 13 where the tube 17 is straight and extends along a long axis from its proximal end to its distal end or is at least partially curved along its length including a dual curve as discussed above. The shaft 6 of FIGS. 20A-20F can be used with an introducer tube 17 having any of a variety of configurations described herein and as shown in FIGS. 1A-1C, 2A-2D, 3A-3D, 4A-4D, 6A-6C, 7A-7B, 12A-12D, 13A-13D, 14A-14D, 15, 16A-16D, and 17A-17B.

The introducer tube 17 can be a stiffer component compared to the elongate shaft 6 extending through it such that the shaft 6 takes on a shape of the introducer tube 17 when retracted inside the introducer tube 17. In an implementation, the introducer tube 17 can be a stainless steel tube and the shaft 6 can be a flexible Nitinol guidewire. As will be discussed in more detail below, the shaft 6 can take on a pre-set shape when extended relative to the introducer tube 17, but once retracted relative to the housing 13 to enter the lumen of the introducer tube 17, the shaft 6 can take on the shape of the introducer tube 17. For example, at least a portion of the introducer tube 17 can be relatively straight and extend along a single longitudinal axis A. The shaft 6, which can include a curved portion 11, can take on a straightened and biased condition. Alternatively, the curvature of the introducer tube 17 can be similar the curvature of the shaft 6 so that retraction of the shaft 6 into the introducer tube 17 does not substantially bias the shaft 6.

The introducer tube 17 can be sized so that the tissue engager 10 upon full retraction of the shaft 6 relative to the introducer tube 17 remains external to the lumen 19. The tissue engager 10 can bottom out against the distal edge 27 of the introducer tube 17 (see FIGS. 7A-7B). In other implementations, the introducer tube 17 (and/or tissue engager 10) is sized so that the tissue engager 10 can be withdrawn fully inside the lumen 19 when the shaft 6 is fully retracted. In still further implementations, the introducer tube 17 can have a size smaller than a maximum outer diameter of the tissue engager 10, but is configured to accommodate the maximum outer diameter, such as by expanding or otherwise changing shape, upon full proximal retraction of the shaft 6 into the lumen 19. For example, the distal end region of the introducer tube 17 can incorporate one or more slits or slots through its wall so that as the tissue engager 10 is retracted and abuts against the distal edge 27 of the introducer tube 17, the walls of the introducer tube 17 flex outward or otherwise move to enlarge a lumen size of the introducer tube 17 to fully envelope the tissue engager 10. When the tissue engager 10 is fully enveloped within the lumen 19 of the introducer tube 17, the distal end 27 of the introducer tube 17 can be inserted through the trabecular meshwork to initiate the disruption. The curved distal end region 23 of the introducer tube 17 can facilitate smooth entry into (or onto the outer wall of) Schlemm's canal.

Figure 15:
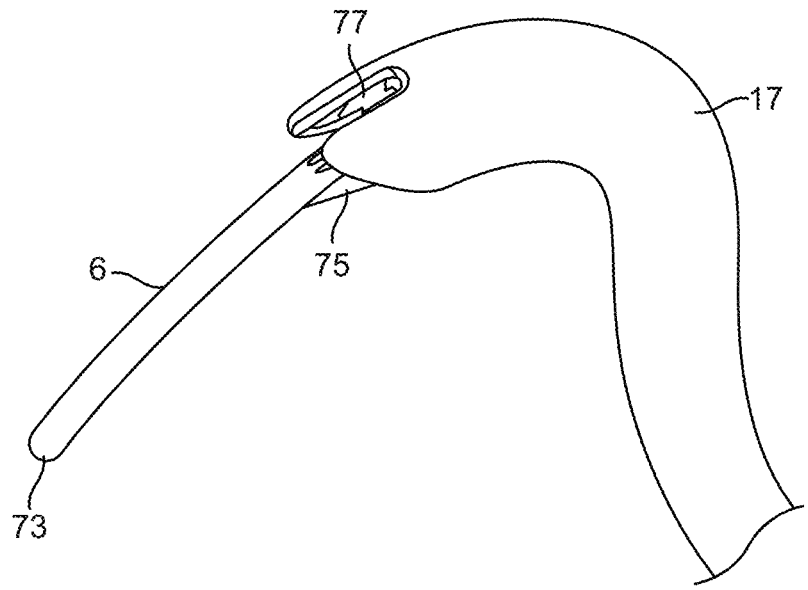
FIG. 15 is a perspective view of an implementation of a dual curve introducer tube for use with any of the devices described herein and having a slot formed in a distal end to receive a tissue disruptor upon retraction of the shaft.

FIG. 15 illustrates an implementation of an introducer tube 17 having a milled slot 77 formed in a distal end of the tube 17. The slot 77 can be positioned on an outer curvature of the tube 17 so as to allow a tissue disruptor 75 positioned on a corresponding outer curvature of the shaft 6 to be fully retracted inside the tube 17. The slot 77 can be additionally or alternatively positioned on the inner curvature of the tube 17. The length of the slot 77 can be sufficient to receive a length of the tissue disruptor 75 in order to fully conceal any sharp edges of the disruptor 75 projecting radially outward from the shaft 6. A shaft 6 having more than a single tissue disruptor 75 on a radially outer surface covering a distance of the shaft 6 can be received within a slot 77 having a corresponding length sufficient to receive each of the disruptors 75 so that any sharpened edges of the disruptors are concealed within the introducer tube 17. The disruptor 75 projecting radially inwardly from the shaft 6 can be received within the bevel of the distal end of the tube 17 forming the distal opening. Thus, the bevel length of the tube 17 can be sufficient to receive the disruptor 75 on the radially inner surface of the shaft 6. Where the radially inner surface of the shaft 6 incorporates a plurality of disruptors 75 positioned end to end with one another along a length of the shaft 6, the bevel length may be insufficient to contain them. An additionally slot 77 can be incorporated at the heel of the bevel so that the additional disruptors 75 on the shaft 6 can be received by the bevel and the slot 77. Any of a variety of introducer tubes 17 described herein can incorporate the slot 77 including those shown in FIGS. 1A-1C, 2A-2D, 3A-3D, 4A-4D, 6A-6C, 7A-7B, 12A-12D, 13A-13D, 14A-14D, 15, 16A-16D, and 17A-17B.

The outer diameter of the introducer tube 17 is preferably small enough to insert through a corneal incision without causing problems with the incision or requiring the incision to be too large. The outer diameter of the introducer tube 17 is generally as small as possible, but not so small that it interferes with movement of the shaft 6 extending through its lumen 19. Thus, the introducer tube 17 can be sufficient in size to receive the shaft 6. The smaller the outer diameter of the shaft 6, the smaller the outer diameter of the introducer tube 17 can be. In some implementations, the outer diameter of the introducer tube 17 is at least about 0.60 mm up to about 1.2 mm.

Again with respect to FIGS. 1A-1C and 2A-2D, the shaft 6 operatively coupled to the housing 13 extends through the lumen of the introducer tube 17. The shaft 6 is configured to move relative to the housing 13 upon actuation of the one or more actuators 25 on the housing 13 to disrupt tissue of the eye with a tissue engager 10 positioned near a distal end region of the shaft 6. The shaft 6 of any of a variety of configurations can be coupled to the housing 13 and actuators 25 as described herein.

The shaft 6 can be a flexible wire, such as a Nitinol guidewire or Nitinol tube, having a pre-set curved shape forming a curved portion 11 having a radial curvature (see FIGS. 5A-5B). In other implementations, the shaft 6 is a flexible ribbon of Nitinol having a pre-set curved shape forming a curved portion 11 having a radial curvature (see FIGS. 18A-18C, 19A-19C, 20A-20F). The curved portion 11 can form a semi-circle having a contour or assume a radius of curvature that is similar to the limbus architecture of the eye. The radial curvature can approximate a circle having a diameter of 5-20 mm, 8-18 mm, or about 12 mm. The radial curvature of the shaft 6 is preferably greater than 6 mm, but can be between 5-20 mm, or between 5-9 mm, or just at about 7.5 mm. In some embodiments, the radial curvature of the shaft 6 can be greater than the curvature of the limbus for sub-limbal gonio modification of the scleral wall. The diameter of the arc span of the flexible shaft 6 may have a memory shape that is at least about 10 mm, at least about 11 mm, or at least about 12 mm in diameter. In some implementations, the diameter of the arc span of the flexible shaft 6 may have a memory shape slightly exceeding the diameter of the average eye limbus or about 13 mm in diameter. The slightly larger diameter can allow for the shaft 6 to impart a slight radially outward force on the eye tissue as the shaft 6 is extended relative to the housing 13 and travels along the anterior angle. The shaft 6 can abut against the firm, outside scleral wall so that the outer wall further guides the device 2 as the tissue engager 10 is advanced distally. The curved portion 11 of the shaft 6 can extend for an angle of greater than 135 degrees, greater than 160, greater than 180 degrees, greater than 200 degrees, greater than 240 degrees or more. The curved portion 11 can extend for an angle of between 160 and 200 degrees.

Again with respect to FIG. 5A, a central plane CP can be defined as a plane on which the advancing direction AD lies and that includes the shaft 6 at the connection of the shaft 6 to the tissue engager 10. The central plane CP can also be defined as the plane on which the advancing direction AD lies and that is positioned on a centerline of the tissue engager 10 when viewed along the advancing direction AD. The central plane CP can also be defined as the plane containing the circular shape of Schlemm's Canal. The shaft 6 can be a flexible memory shaped material configured to substantially conform to the contour of the eye. The curved portion 11 also defines the plane of curvature in use. The shaft 6 can have a curved shape that lies in the plane of curvature in use that is aligned with the plane on which the circular Schlemm's Canal lies.

Still with respect to FIG. 5A, the elongate shaft 6 may be flexible and resilient to provide a "soft" feel during use with the shaft 6 being elastically deflected and deformed in use. Specifically, the shaft 6 may be resilient relative to forces exerted against the tissue engager 10 in the advancing direction AD. However, the shaft 6 is not so flexible that it is not pushable along eye tissue. For example, the shaft 6 may be made of a metal and may be a superelastic material, such as Nitinol, which provides a wide range of elastic response. The shaft may be 0.15 mm diameter Nitinol wire and may be 0.10 to 0.25 mm. The shaft can be a spiral-cut Nitinol tube having a slightly larger diameter than the Nitinol wire, for example about 0.175 mm. The shaft can be a laser-cut flat sheet of Nitinol, for example, between 100-150 microns thick and about 0.010-0.015 cm wide. Where the shaft 6 is referred to herein as a "wire" it should be appreciated the shaft 6 may also be a tube or ribbon. The shaft 6 can have a light spring load in the advancing direction AD as it is advanced. The curved portion 11 of the shaft 6 can also provide a resilient response in a direction perpendicular to the advancing direction AD and lying in the plane of curvature CP. The shaft 6 may develop a spring load in the advancing direction and in a radially outward direction relative to the axis of the eye. In this manner, the radially outward force can cause the tissue engager 10 coupled to a distal end region of the shaft 6 to slide against the sclera (i.e., outer wall of Schlemm's Canal) to stabilize the tissue engager 10. Stated another way, as the tissue engager 10 is moved through the trabecular tissue, the shaft 6 can be shaped to apply a radially outward force on the tissue relative to the axis of the eye. While the shaft 6 is pushable and can apply a radially outward force, the resilient nature of the shaft 6 can limit or prevent excessive forces or displacement from being applied to the eye inadvertently.

The shaft 6 can have a stiffness, resiliency or spring constant to be operable when moving the tissue engager 10 to displace the tissue to be removed. The shaft 6 may have a stiffness in the advancing direction of less than 20 N/mm, less than 10 N/mm or even less than 5 N/mm, when the tissue engager is moved to displace the tissue. The shaft 6 may also have a stiffness in a direction perpendicular to the advancing direction and lying the plane of curvature of less than 20 N/mm, less than 10 N/mm or even less than 5 N/mm, which presses the main body against the eye when moving the tissue engager to displace the tissue. When the tissue engager 10 is positioned relative to the anterior angle, the perpendicular force can press the tissue engager 10 against the sclera. The shaft 6 may have the desired stiffness characteristics while the shaft 6 is able to change the angle of the tissue engager 10 by at least 45 degrees and may be at least 90 degrees (by extension or retraction of the shaft 6). The angle of the shaft 6 can be changed by extending the shaft 6 from the introducer tube 17. The shaft 6 can extend relative to the tissue engager 10 at an angle of greater than 90 degrees, or even greater than 135 degrees, and may be 160 to 200 degrees or even 160 to 240 degrees, relative to the advancing direction AD. The extension can be at least 30 degrees up to about 360 degrees, preferably about 120-180 degrees. Complex movements of the housing 13 can be reduced due to the flexibility of the shaft 6 compared to devices having rigid shafts, which require the shaft angle to be changed as the device is advanced through the eye. Non-flexible (rigid) shafts are limited to partial pivot angulation at the site of ab-interno entry into the anterior chamber (between 10-120 degrees only). Instead, the flexible shaft 6 of the devices described herein may be made of elastic or superelastic alloys, such as Nitinol, or other suitable metal or material, such as polymers, that provide sufficient flexibility to access the entire internal circumference of the anterior chamber and the gonio anatomy. Movements with a rigid shaft can be challenging given the limited degrees of freedom and movement for devices introduced into the eye. The devices described herein reduce and can even eliminate the need to change the angle of the shaft/housing when disrupting the tissue at the anterior chamber angle.

The elongate shaft 6 may have a circular or non-circular cross-sectional shape, such as a square or rectangular cross-sectional shape. FIGS. 5B, 6C, 7B, 14E, 15, and 16E illustrate shafts 6 with circular cross-sectional shape whereas FIGS. 18A-18C, 19A-19C, and 20A-20F illustrate non-circular cross-sectional shaped shafts 6. The shaft 6 can have an outer dimension of 100-1100 microns. The shaft can be a spiral-cut Nitinol tube having a slightly larger outer diameter than the Nitinol wire, for example about 0.175 mm. The non-circular cross-sectional shape can have a minor axis and a major axis, the major axis being within 30 degrees, and may be within 15 degrees, of perpendicular to the central plane. The major axis may be at least 20% larger than the minor axis. The minor axis may be less than 250 microns while the major axis may be larger than 250 microns. The shaft 6 may have an effective radius of 40 to 400 microns, or 50-300 microns, although different sizes and shapes may be used. The shaft 6 may be made of a metal, such as a superelastic material (Nitinol). The effective radius is the equivalent radius for a circle having the same cross-sectional area for a non-circular cross-section (such as elliptical, square, or rectangular).

The shaft 6 can be a Nitinol tube having one or more cuts along its length to provide flexibility. FIG. 16E shows a spiral-cut Nitinol tube forming the shaft 6. The spiral cuts need not extend along the entire length of the shaft 6 and can be positioned along one or more regions between the proximal and distal ends. The spiral-cut tube can allow for one or more tissue engagers 10 to be coupled to an inner and/or outer curvature of the shaft 6. For example, FIG. 16E shows a single disruptor 75 positioned on the inner curvature of the spiral-cut tube shaft 6 and a second disruptor 75 positioned on an outer curvature of the shaft 6. The shaft 6 can incorporate additional disruptors 75 positioned proximal to the single disruptor 75, if desired, or additional disruptors 75 proximal to the second disruptor 75 positioned on the outer curvature.

The shaft 6 can have a variable stiffness by changing a length of the shaft 6 extending from the housing 13, such as a length extending outside the lumen 19 of the introducer tube 17. The variable stiffness of the shaft 6 can be changed by at least at factor of 10 when moving between a first working position and a second working position so that the first position with the smallest stiffness is at least 10 times smaller than the second position with the larger stiffness with both positions being operable to displace the tissue. The variable stiffness may be provided by retracting and extending the shaft 6 to change a length of the shaft 6 extending from the housing 13 outside the introducer tube 17. The first and second working positions may change the orientation of the distal end 73 of the shaft 6 by at least 45 degrees relative to the housing 13. The shaft 6 cross-section may be constant or may increase proximally to maintain a more consistent stiffness. For example, the stiffness may vary less than 30% for a curved portion that is extended and retracted to change the angle of the shaft 6 by at least 45 degrees.

Again with respect to FIGS. 5A-5B, the tissue engager 10 (which can include multiple disruptors on the inner and/or outer curvatures of the shaft 6) is positioned near the distal end region 74 of the shaft 6. The tissue engager 10 can be formed as a non-cutting, blunt element projecting away from the longitudinal axis or the center of the shaft 6 that is configured to engage tissue in the anterior angle, such as the trabecular meshwork, as the shaft 6 is advanced out from the introducer tube 17 along the anterior chamber angle. The tissue engager 10 can slide along an inner wall (or along an outer wall) of the Schlemm's canal as the trabecular tissue and thus, Schlemm's canal is disrupted. The tissue engager 10 may be a blunt feature sized to span the trabecular meshwork to form a continuous non-cutting trabeculorhexis so that the tissue engager 10 stretches and tears the trabecular meshwork fibers as it follows the contour of the eye and may disinsert some of the tissue at the origin. The tissue engager 10 can be introduced into an anterior chamber of an eye positioned adjacent tissue in the anterior chamber angle, e.g., an inner or outer wall of Schlemm's Canal. The tissue engager 10 can be moved by advancing the shaft 6 in an advancing direction AD and parts of the trabecular meshwork removed, such as by bluntly tearing, stripping, and/or disinserting the trabecular meshwork tissue.

Figure 6C:
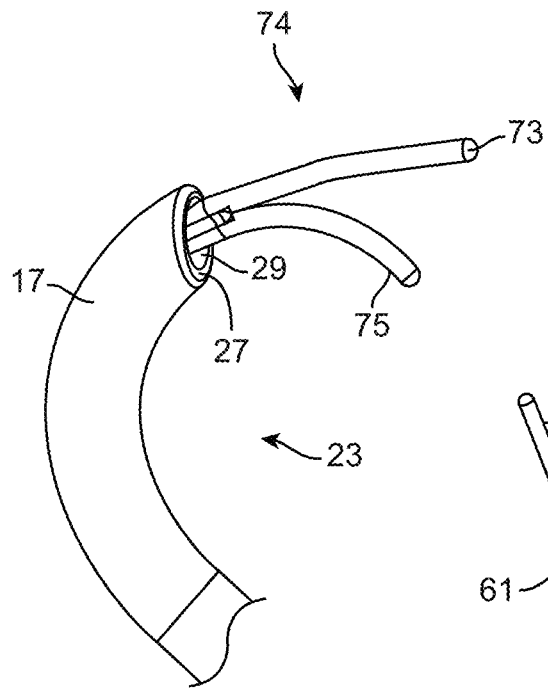
FIG. 6C is a detail view of the tissue engager of the device of FIG. 6A.
Figure 7A:
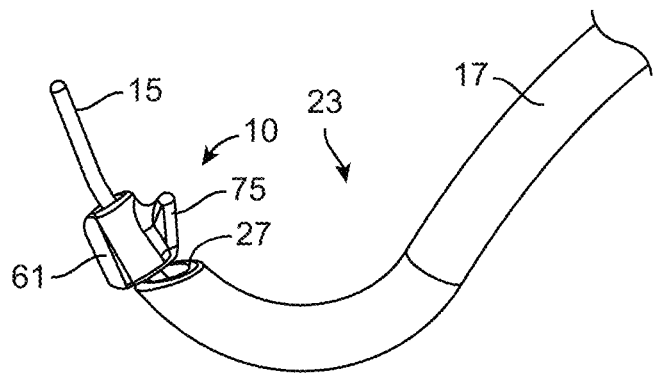
FIGS. 7A-7B are distal end views of a device having a tissue engager.
Figure 7B:
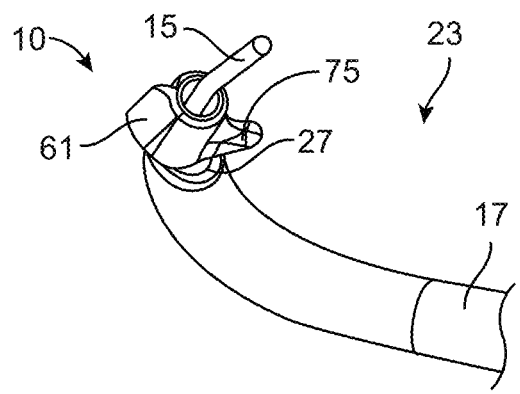

The tissue engager 10 may be coupled to the shaft 6, such as by welding, gluing, or otherwise attaching the tissue engager 10 near the distal end of the shaft 6. FIGS. 6A-6C, 7A-7B, 14E, and 15 show other implementations of the tissue engager 10 attached at the distal end region 74 of the shaft 6. Any of a variety of tissue engagers described herein (e.g., FIGS. 1A-1C, 2A-2D, 5A-5B, 6A-6C, 7A-7B, 8A-8D, 9A-9D, 14A-14G, 15, 16A-16E, 18A-18C, 19A-19C, and 20A-20F) can be incorporated on any of a variety of shafts 6 described herein and paired with any of a variety of introducer tubes 17 (FIGS. 1A-1C, 2A-2D, 3A-3D, 4A-4D, 6A-6C, 7A-7B, 12A-12D, 13A-13D, 14A-14D, 15, 16A-16D, 17A-17B). Although the structural configuration can vary, the tissue engager 10 can be an enlarged feature coupled to or projecting from the distal end region 74 of the shaft 6 and having a disruptor 75 projecting inwardly (and/or outwardly) from the shaft 6 to engage with the trabecular tissue (and/or outer wall). The disruptor 75 can be coupled directly to or formed in the shaft 6 so that it projects inwardly relative to the eye and the advancement direction as the shaft 6 is advanced as shown in FIG. 6B. In this implementation, the disruptor 75 can be a short segment of wire that is welded directly to the flexible wire forming the shaft 6. The disruptor 75 can be formed as a triangular-shaped segment of material welded to one or more regions of the shaft 6 (see FIGS. 14E and 15). The disruptor 75 can be formed into a sharpened edge facing an inner curvature or the edge facing the inner curvature can be squared off or otherwise blunt or dull rather than a sharp blade edge. The disruptor 75 can reduce the size of the diameter associated with attaching a discrete part on the wire shaft 6.

The tissue engager 10 need not be physically coupled to the shaft 6 and can be integrally shaped, formed, or cut into the material forming the shaft 6 as discussed above with regard to the micromachined shaft 6 shown in FIGS. 18A-18C, 19A-19C, and 20A-20F. In other implementations, the shaft 6 may have a bent portion near a distal end of the curved portion 11 that projects inwardly forming a tissue engager integrally formed with the shaft 6. The bent portion can extend inwardly relative to the curved portion 11 by a distance of 200 to 800 microns. The bent portion may form an angle with the elongate shaft 6 of 10 to 150 degrees. Additional implementations of a tissue engager 10 are described in U.S. Pat. No. 10,905,591, which is incorporated herein by reference in its entirety.

FIGS. 8A-8D and 9A-9D illustrate other implementations of tissue engagers 10. The main body of the tissue engager 10 can include a first sidewall 14 on one side and a second sidewall 16 on an opposing lateral side that extend from a tissue engaging surface 31. The tissue engager 10 can have an upper surface 18 and a lower surface 20 with the lower surface 20 configured to be positioned adjacent the outer wall of Schlemm's Canal so that the tissue engager 10 can slide against the sclera or outer wall of Schlemm's Canal. The tissue engager 10 has a height H measured perpendicular to the advancing direction AD (and transverse to the wall of Schlemm's Canal in an essentially radially inward direction relative to the circular shape of the canal) from the upper surface 18 to the lower surface 20. The tissue engager 10 has a width W measured perpendicular to the advancing direction (and to the height H). The height H and width W of the tissue engager 10 are intended to capture and gather the trabecular meshwork. In this manner, the gathered tissue is less likely to tear or rip between the first and second sidewalls 14, 16 compared to the tissue along the first and second sidewalls 14, 16 as the lower surface 20 slides against a wall of Schlemm's canal or the sclera. The lower surface 20 may be laser etched, chemical etched or ground to provide a desired texture.

The height H between the upper surface 18 spaced apart from the lower surface 20 can be at least 150 microns and may be 500 to 1200 microns or 500 to 800 microns or 250 to 700 microns or 400 to 700 microns with alternative ranges for being 250 to 550 microns and may even be 250 to 450 microns at a center of the upper surface 18 with the center of the upper surface 18 being the furthest part of the upper surface 18 from the lower surface 20. The tissue engager 10 can have a height H that is less than 600 microns and may be 50-500 microns. Any suitable height is considered depending on the desired amount of trabecular meshwork to be stripped. The first sidewall 14 and the second sidewall 16 may have a height of at least 150 microns and may be 500 to 800 microns (measured perpendicular to the advancing direction AD) and a length of 200-500 microns (measured along the advancing direction AD), or a length of 180 to 220 microns. The first sidewall 14 and the second sidewall 16 may also form an angle with the central plane CP of less than 45 degrees and may even be less than 20 degrees. The first sidewall and the second sidewall extend from the tissue engaging surface 31 on opposing lateral sides of the tissue engaging surface 31. The width W between the sidewalls 14, 16 can be at least 300 microns or at least 400 microns and may be 300 to 700 microns, or 450-850 microns or 500-700 microns, or 50 to 500 microns.

Figure 8A:
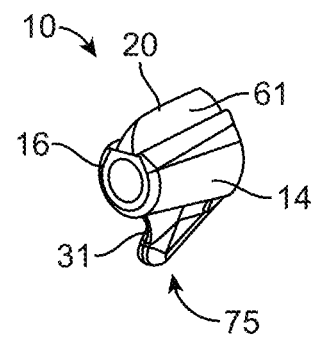
FIG. 8A is a perspective view of an implementation of a tissue engager.
Figure 8B:
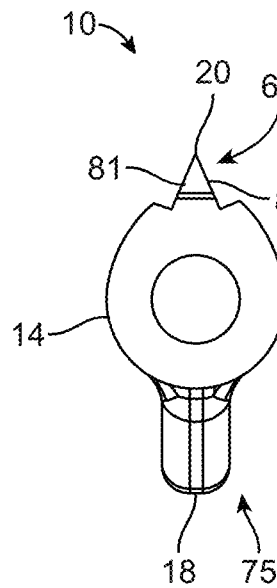
FIG. 8B is a proximal end view of the tissue engager of FIG. 8A.
Figure 8C:
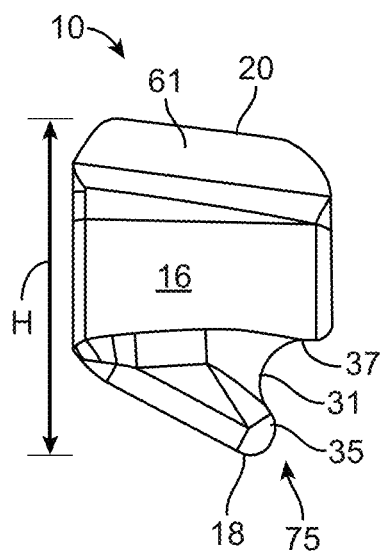
FIG. 8C is a side view of the tissue engager of FIG. 8A.
Figure 8D:
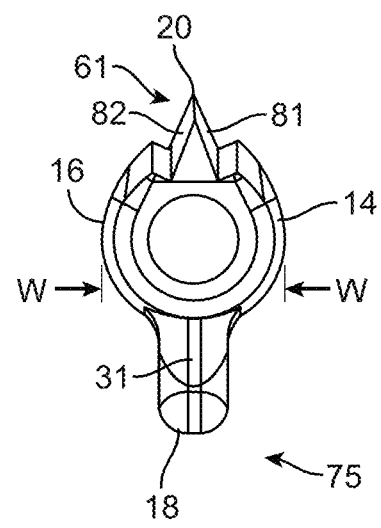
FIG. 8D is a distal end view of the tissue engager of FIG. 8A.
Figure 9A:
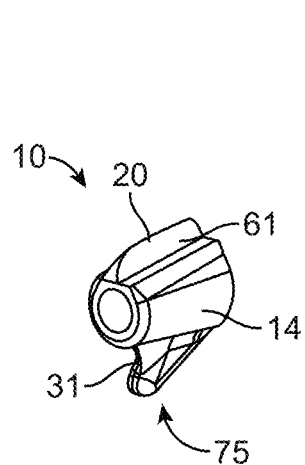
FIG. 9A is a perspective view of an implementation of a tissue engager.
Figure 9B:
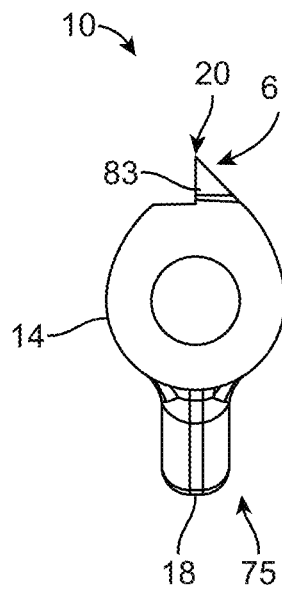
FIG. 9B is a proximal end view of the tissue engager of FIG. 9A.
Figure 9C:
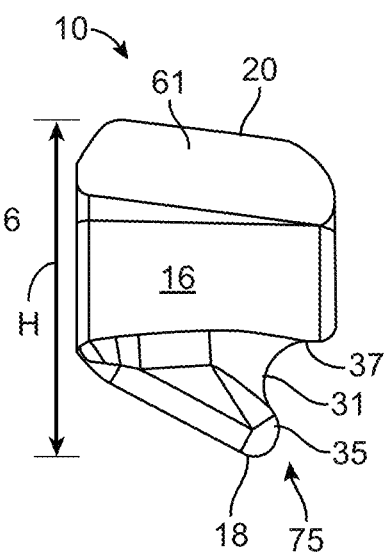
FIG. 9C is a side view of the tissue engager of FIG. 9A.
Figure 9D:
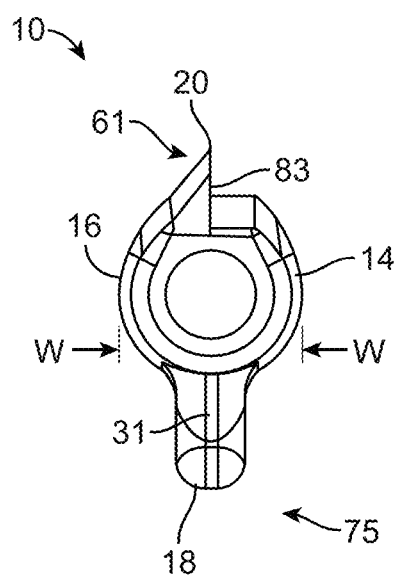
FIG. 9D is a distal end view of the tissue engager of FIG. 9A.

Still with respect to FIGS. 8A-8D and 9A-9D, the tissue engaging surface 31 may form a concave region when viewed perpendicular to the advancing direction (see FIGS. 8C and 9C). The concave portion tissue engaging surface 31 can have an upper lip 35 and a lower lip 37 that may help gather and compress tissue together as the device 2 is advanced. The upper lip 35 can form an angle of less than 90 degrees (and may be 30-70 degrees) with the advancing direction AD when viewed perpendicular to the advancing direction while the lower lip 37 may form an angle of 0-30 degrees with the advancing direction AD when viewed perpendicular to the advancing direction AD. The tissue engaging surface 31 can have a depth of at least 50 microns measured perpendicular to a line extending between the upper lip 35 and the lower lip 37 of the tissue engaging surface 31. Stated another way, the tissue engaging surface 31 can form a recess having a recess depth measured in the advancing direction and the recess depth can be at least 100 microns, at least 200 microns, or 300-600 microns. The recess can have a recess height measured perpendicular to the advancing direction and parallel to the central plane that can be at least 200 microns and may be 300-600 microns. The recess may also have a recess width measured perpendicular to the advancing direction AD and to the central plane CP that can be 300 to 700 microns and may be 400 to 600 microns.

The tissue engager 10 can gather tissue and displace the tissue with a blunt non-lacerating engagement. As the tissue engager 10 moves the gathered tissue forward, tissue along the first and second sidewalls 14, 16 can be sheared and/or torn without cutting or the need for a cutting element. Stated another way, the tissue engager 10 can compress and gather tissue to bunch the tissue between the upper lip 35 and the lower lip 37 in a direction perpendicular to the advancing direction AD and lying in the central plane CP. The tissue engager 10 compresses and gathers tissue while the tissue is torn and sheared along the first and second sidewalls 14, 16 during displacement of the gathered tissue. The tissue engager 10 may be moved through the trabecular meshwork continuously along any angular extent, such as 10-360 degrees or 30 to 180 degrees of a circumference of an eye (or of the Schlemm's canal). The tissue engager 10 shears tissue along the first sidewall 14 and the second sidewall 16 due to displacement of tissue gathered by the tissue engager 10. The tissue engager 10 may also lack any piercing elements and may tear the tissue without cutting or ablating although numerous aspects may be practiced with the tissue engager 10 cutting tissue as mentioned above. The tissue engager 10 can be a blunt, non-incisional probe and can displace the trabecular meshwork tissue to bluntly disinsert the trabecular meshwork tissue.

The tissue engaging surface 31 can have an orientation that is within 15 degrees, and may be within 10 degrees, of perpendicular to the advancing direction AD. The tissue engaging surface 31 can have a width W of at least 400 microns and may be 500-800 microns. The tissue engaging surface can have a height H of at least 300 microns, at least 400 microns, at least 500 microns or may be 550-1200 microns or even 800 to 1200 microns. The width W of the tissue engaging surface helps to gather an amount of tissue ahead of the tissue engaging surface. In this manner, the tissue is ripped/torn/sheared from the native tissue due to displacement of the tissue gathered ahead of the tissue engaging surface. Displacing tissue in this manner encourages the tissue to be torn on both lateral sides thereby releasing a strip of the trabecular meshwork. Thus, stated another way, the tissue engaging surface displaces an amount of tissue having a width of at least 300 microns and may be at least 400 microns.

In some implementations, the device 2 can include a distal probe 15 projecting distally from the tissue engager 10 (see FIGS. 5A-5B, 6, 7A-7B). The probe 15 can be integral with or formed by the distal end of the shaft 6 as shown in FIGS. 5A-5B and 6 or can be formed as part of the tissue engager 10. In some implementations, the tissue engager 10 is coupled to a region of the shaft 6 that is proximal to the distal-most end 73 of the shaft 6 such that the distal probe 15 is formed by the segment of the shaft 6 that extends distal to the tissue engager 10. The probe 15 can serve as a probing canal engagement front end and can be blunt and non-incisional. The probe 15 can guide the device along Schlemm's canal as the shaft 6 is advanced and the tissue engager disrupts the trabecular meshwork. The probe 15 can insert within Schlemm's Canal prior to disruption of the trabecular meshwork as the tissue engager 10 is advanced along the angle.

The tissue engager 10 can include a frustoconical surface that tapers down towards the outer diameter of the probe 15 (which may be an extension of the shaft 6 as discussed above). The probe 15 can have an outer diameter that is about 100-280 microns. The shaft 6 can have an outer diameter that is about 100-800 microns. The probe 15 can be designed for intracanalicular placement/deployment and guided traction along the canal while the shaft 6 can be designed to advance the probe 15 while remaining outside the canal.

The probe 15 can be elongate so that at least a portion of the device 2 inserts within Schlemm's Canal prior to the tissue engager 10 disrupting the trabecular meshwork and eliminating the canal. For example, the probe 15 can extend distally from the tissue engager 10 by a distance of 300 to 5000 microns, or by a distance of 30 microns to 500 microns, although the probe 15 may be shorter or longer. The probe 15 may be a piece of formed sheet metal and extend distally from the tissue engager 10 by a distance of 30-500 microns. The probe 15 also can be very short so that substantially no portion of the device 2 inserts within Schlemm's Canal prior to the tissue engager 10 disrupting the trabecular meshwork and eliminating the canal. The device 2 may also have no distal, probe 15 that inserts within Schlemm's Canal such that the tissue engager 10 essentially disinserts or scrapes away the trabecular meshwork without any entry of Schlemm's by the device 2. Thus, the tissue engager 10 need not be fully or even partially inserted within the Schlemm's Canal, such as with a distal probe 15, in order to disrupt tissue.

The tissue engager 10 can disrupt the trabecular meshwork from the anterior chamber angle as it is advanced around the eye without entering the canal. Alternatively, the tissue engager 10 can disrupt the sclera following removal or disinsertion of the trabecular meshwork. In other words, because the Schlemm's Canal has already had one of its walls disrupted (i.e., the inner wall), there is no "canal" to be cannulated or catheterized. Rather, an open channel has been formed revealing the scleral wall ab interno so that the tissue may be engaged by one or more features of the devices described herein. Thus, the ab interno method can involve a "non-canal" or "outside the canal" sort of gonio-intervention or modification of the anterior angle of the eye. This non-catheterized, non-cannulated access to the scleral wall in the anterior angle provides a greater flexibility in the sort of interventions that can be performed because there is no need for canal catheterization. The tools for the intervention described herein can be larger than tools that are required to fit within the Schlemm's Canal between the trabecular meshwork and the scleral wall, but still sufficiently small for ab interno insertion through a self-sealing corneal incision or puncture.

The various surfaces and dimensions described herein for all embodiments shall be defined by the view associated with particular surface or orientation. When considering a rectangular-shaped cross-section each of four defined sides may be well defined. When a circular cross-sectional shape is used, it is understood that the definition of upper surface and lower surface would subdivide the circular cross-section into two half circles. Similarly, the lateral walls would subdivide into two half circles which means that each part of the surface may define two surfaces since the surfaces are exposed in two orientations and contribute to both width and height.

Again with respect to FIGS. 7A-7B, the tissue engager 10 can additionally or alternatively include a cutting element 61 on the outer-facing lower surface 20. The cutting element 61 can cut a circumferential slit in the canal outer wall as the device is advanced. The tissue engager 10 may simultaneously gather trabecular tissue with the disruptor 75 so that the tissue stretches and tears along a first sidewall 14 and a second sidewall 16 as described herein and cut scleral tissue with the cutting element 61. The device 2 may also operate without trabeculorhexis and may be practiced with the cutting element 61 only. The device 2 may also operate to perform a first method step to disrupt an inner wall of Schlemm's Canal (i.e., the trabecular meshwork) with disruptor 75 and as a second method step perform modification of the outer wall (i.e., sclera) with the cutting element 61. Thus, the tissue modifications of the inner and outer walls of Schlemm's canal can be performed simultaneously with cutting element 61 and disruptor 75 or as sequential steps with the different tools. The cutting element 61 may also be referred to herein as a tissue disruptor 75 on the radially outer surface of the shaft 6.

The cutting element 61 can extend from or be positioned near a lower surface 20 of the tissue engager 10. The cutting element 61 can form the lower surface 20 of the tissue engager. The cutting element 61, in use, is directed in a radially outward direction as defined by the circular shape of the eye (and the central axis CA of the eye). The cutting element 61 can be coupled to the tissue engager along the lower surface 20 that can be pressed against the wall of the canal. The cutting element 61 may be oriented to form a cut that is essentially radially outward RO direction relative to the central axis of the eye. The cutting element 61 may be oriented to form a cut with an angle AC which is within 60 degrees, 30 degrees, or even within 15 degrees, of the radially outward RO direction defined by the circular shape and central axis CA of the eye.

The cutting element 61 is capable of forming a continuous cut in the outer wall of Schlemm's canal to increase an effective size of Schlemm's canal. The effective size is increased since the slit increases the potential enclosed volume of the canal. Any length of slit may be formed and the device is capable of forming a continuous cut through at least 45 degrees, and may be at least 90 degrees, of Schlemm's canal in use. The cutting element 61 may extend from the surface that slides against the canal wall and may help stabilize the cutting element 61. The shaft 6 is also capable of developing the spring response described herein that may also provide advantages when advancing the cutting element 61 through the canal wall. The cutting element 61 can be used to modify not just the outside wall of Schlemm's canal, but anywhere along a band of the eye extending from the ciliary body to the limbus depending on a rotational angle of the tissue engager 10.

The cutting element 61 can be used to form an elongate (in the circumferential direction) slit that increases the available surface area available for fluid transfer. The slit also effectively shortens the fluid path since the fluid path is generally radially outward and the slit is formed generally in a radially outward direction. The tools described herein may be also practiced without removing the trabecular meshwork in a canaloplasty procedure. The tissue engager and cutting element can be reduced in size and delivered through a cannula to form one or more circumferential slits in the radially outer (sclera) wall. The elongate slit may provide improvement in fluid flow as a primary canaloplasty therapy for the reasons discussed above. Although the devices are described as capable of performing trabeculorhexis rather than cutting, it should also be appreciated a cutting element can be incorporated rather than one that rips/strips/tears the tissue. For example, all aspects of the shaft 6 may be practiced with the tissue engager 10 cutting tissue.

FIGS. 8A-8D illustrate a first implementation of the cutting element 61. The cutting element 61 can be formed by machining the lower surface 20 of the tissue engager 10 at two locations forming a 45 degree angle wedge faces 81, 82 that taper to a sharpened edge when viewed from a proximal end (see FIG. 8B). FIGS. 9A-9D illustrate a second implementation of the cutting element 61. The cutting element 61 can be formed by machining the lower surface 20 of the tissue engager 10 at a single location forming a flat face 83 to the cutting element 61 that together with the second sidewall 16 forms a single sharpened edge (see FIG. 9B).

Figures 16A, 16B:
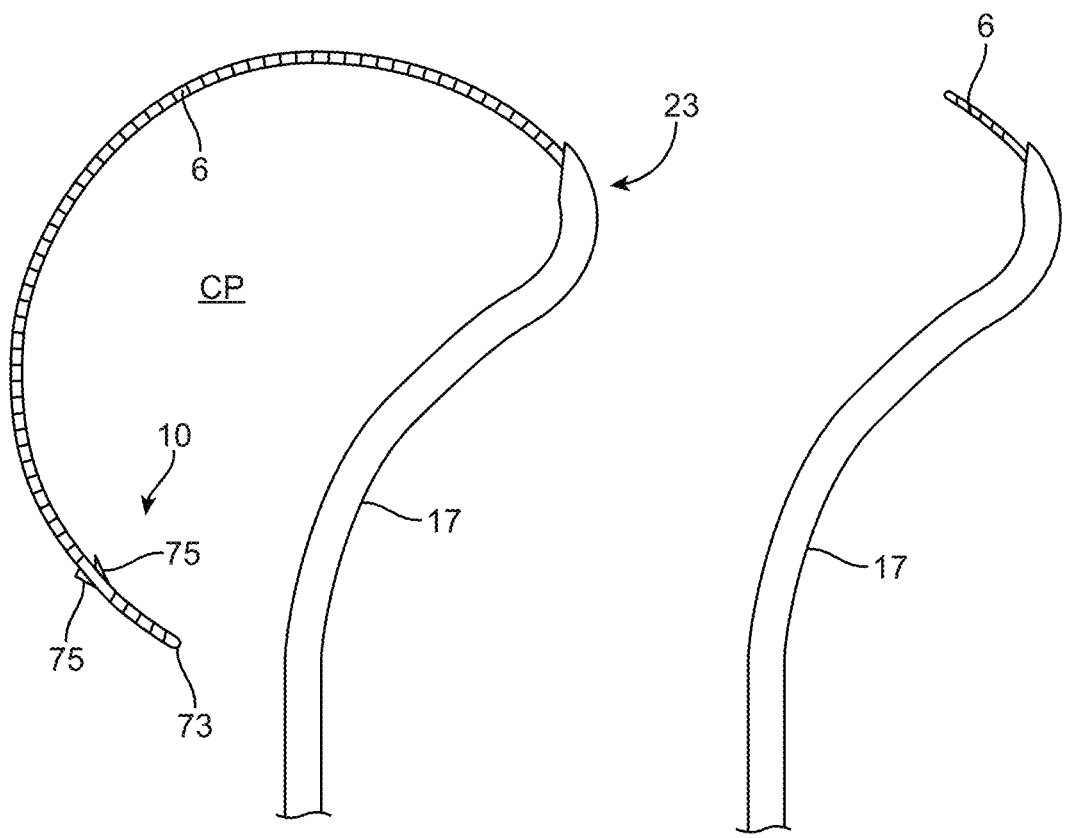
FIG. 16A is a side view of an implementation of a dual curve introducer tube for use with any of the devices described herein with the shaft extended.
FIG. 16B is a side view of the introducer tube of FIG. 16A with the shaft retracted.

FIGS. 16A-16D illustrates another implementation of the introducer tube 17 having two curvatures. FIG. 16A shows the shaft 6 extended out from the introducer tube 17 and FIG. 16B shows the shaft 6 retracted within the introducer tube so that the tissue disruptor 75 is substantially contained within the lumen of the tube 17. FIGS. 16C-16D are the same as FIGS. 16A-16B rotated slightly to illustrate the distal opening 29 from the lumen 19. The shaft 6 can be a spiral-cut Nitinol tube having at least one tissue disruptor 75 welded near a distal end region of the shaft 6 proximal of the distal-most end 73. The tissue disruptor can be a protrusion extending radially inwardly from the shaft and comprise a blunt tissue-engaging surface without any cutting element. The tube may also have two tissue disruptors 75. A first tissue disruptor 75 can be positioned on an inner curvature and a second tissue disruptor 75 can be positioned on an outer curvature of the shaft 6. FIG. 16E is a detailed view of the distal end region of the shaft 6 of FIGS. 17A and 17B. The inner curvature disruptor 75 can have a triangular shape. In some implementations, the disruptor 75 can be sharpened or beveled into a blade or to have a pointed/edged feature. The forward-facing surface of the disruptor 75 on the inner curvature can form an angle with the inner-facing surface of the shaft 6 that is greater than 90 degrees. The proximal-facing surface of the disruptor 75 on the inner curvature can form an angle with the inner-facing surface of the shaft 6 that is less than 90 degrees although the angle can vary and can also be greater than or equal to 90 degrees. The outer curvature disruptor 75 can also have a triangular shape. The forward-facing surface of the disruptor 75 on the outer curvature can form an angle with the outer-facing surface of the shaft 6 that is greater than 90 degrees. The proximal-facing surface of the disruptor 75 on the outer curvature can form an angle with the outer-facing surface of the shaft 6 that is greater than 90 degrees although the angle can vary and can also be less than or equal to 90 degrees. FIG. 16E illustrates an angle between the forward-facing surface of the disruptor 75 and the inner-facing surface of the shaft 6 that is about 150 degrees and an angle between the proximal-facing surface of the disruptor 75 and the inner-facing surface of the shaft 6 that is about 45 degrees. The tissue disruptor 75 for the outer wall can incorporate micro-serrations for outer wall thinning and canaloplasty to improve canalicular/trans-scleral outflow. The shaft 6 can incorporate a single-wall trabeculorhexis goniotomy tip on an inner-facing surface for 180 degree or 360 degree continuous, single-pass guided goniotomy for non-cutting guided disinsertion of the trabecular meshwork. In other implementations as shown in FIG. 16E, the shaft 6 can incorporate a dual-wall total canalotomy serrator for trabeculorhexis-goniotomy and outer wall canaloplasty. The disruptor can be micro-serrated for outer wall thinning/canaloplasty to improve canalicular outflow. The devices described herein can be used as stand-alone treatment or used in combination with phacoemulsification of a cataract.

The device 2 can include features designed to modify the gonio scleral wall after and/or prior to removal/disruption/excision of Schlemm's canal that can include the cutting element 61 or other surface modifying elements on a surface of the shaft 6 or tissue engager 10 that is directed radially outward, including one or more blades, abrasive surfaces, thinning elements, or other structural modifiers of the gonio wall of the eye. The devices described herein need not canal catheterization to access the scleral wall in the angle.

As mentioned above, the housing 13 can include one or more actuators 25 configured to move one or more portions of the device 2. An actuator 25 can be operatively coupled to the shaft 6 such that the shaft 6 can be translated forward and back relative to the housing 13 to extend and retract the shaft 6 from the introducer tube 17. When the shaft 6 is extended in use, the curved portion 11 of the shaft 6 can naturally changes the angle of the tissue engager 10 coupled to a distal end region 74 of the shaft 6 (and the orientation of the longitudinal axis of the shaft 6 at the distal end) relative to the housing 13. The angle can be changed by at least about 45 degrees up to about 180 degrees. The curved portion 11 of the shaft 6 can naturally change the angle of the tissue engager 10 relative to the housing 13 as the shaft 6 is extended longitudinally from the housing 13. The one or more actuators 25 can include a button, slider, dial, or other actuator or combination of actuators.

FIG. 1A illustrates a housing 13 with an actuator 25 that is a slider on an upper surface of the housing that is configured to control extension and retraction of the shaft 6. FIG. 2A illustrates a housing 13 having an additional actuator 25 configured to move the introducer tube 17. The one or more actuators 25 can include a dial 26 on a rear end of the housing 13 configured to rotate the introducer tube 17 in clockwise and counter-clockwise directions. The dial 26 can be formed by a rear section of the housing 13 that rotates around a longitudinal axis of the housing 13 relative to a front section of the housing 13. The rear section can rotate, for example, up to about 180 degrees, and cause the introducer tube 17 to rotate a corresponding around the longitudinal axis. The introducer tube 17 can be rotated in order to create a larger disruption with the tissue engager 10. As an example, a surgeon can first deploy the shaft 6 and the tissue engager 10 from the introducer tube 17 counter-clockwise up to about 180 degrees. The shaft 6 can be withdrawn back inside the introducer tube 17 and the introducer tube 17 turned by 180 degrees relative to the housing 13 using the dial 26. The shaft 6 can then be advanced from the introducer tube 17 clockwise up to 180 degrees. The two advancements in counter-clockwise and clockwise directions can provide up to a 360 degree disruption, if desired. The dial 26 configured to rotate the introducer tube 17 can provide a greater freedom for a user to orient the introducer tube 17 relative to the housing 13 depending on whether a right eye or a left eye is being treated and/or what approach is being used. The orientation of the introducer tube 17 to the housing 13 can be adjusted to suit a user's preferred access angle and location. The dial 26 can allow for any of a variety of incremental degrees of rotation. The dial 26 can provide a smooth feel during rotation or can provide tactile and/or auditory feedback as to the number of degrees the dial 26 has been moved around the longitudinal axis. Any of a variety of actuators 25 and combinations are considered.

The device 2 can be coupled to a source of suction so that aspiration and/or infusion of fluids can be performed through the lumen 19 of the introducer tube 17. Alternatively, tissue and fluids may be removed/delivered using a separate suction device in fluid communication with the lumen 19.

Figure 10A:
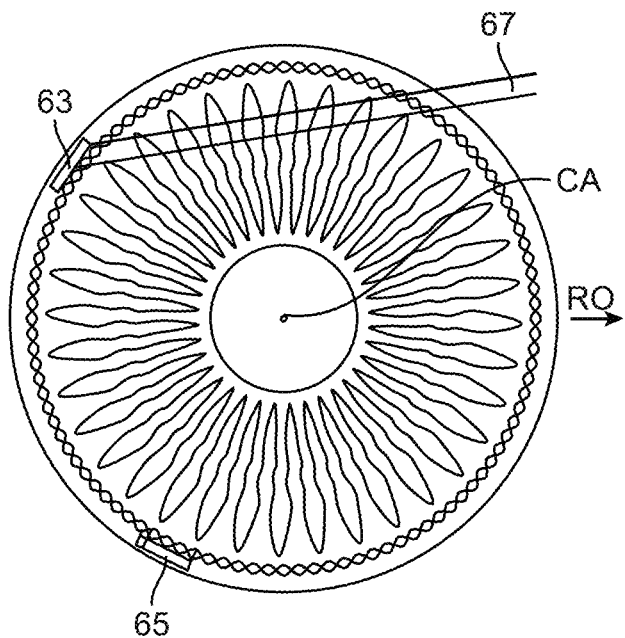
FIG. 10A shows in schematic an entry opening and a terminal opening formed through the trabecular meshwork.
Figure 10B:
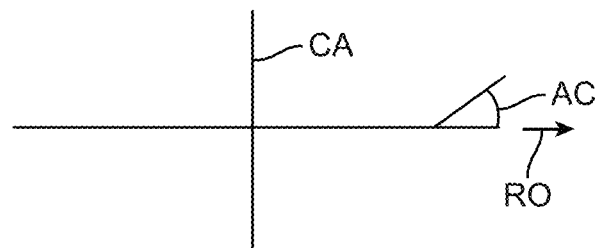
FIG. 10B shows the central axis CA of the eye show in in FIG. 10A.

Use of the devices 2 is now described with reference to the device 2 and FIGS. 10A-10B and FIG. 11. The elongate shaft 6 can be advanced longitudinally from the introducer tube 17 to advance the tissue engager 10 through the trabecular tissue in the following manner. The device 2 is introduced into the eye ab interno using any suitable approach. A corneal incision or puncture can be formed and the distal end of the device 2 inserted through the opening. An entry opening 63 and a first terminal opening 65 can be formed through the trabecular meshwork to Schlemm's canal using a conventional bladed instrument 67 (see FIG. 10A). The introducer tube 17 of the device 2 can then be introduced into the entry opening 63 and the tissue engager 10 advanced toward the first terminal opening 65 by extending the shaft 6 distally from the housing 13 (FIG. 11). As the tissue engager 10 is advanced, the flexible, curved shaft 6 changes the orientation of tissue engager 10 to conform the lower surface 20 of the tissue engager 10 towards the outer wall (i.e., the scleral wall) and the upper surface 18 towards the central axis CA. In this manner, the user may not be required to substantially change the orientation or position of the housing 13 as the tissue engager 10 is advanced.

When the tissue engager 10 reaches the first terminal opening 65, a first strip of tissue has been released and removed to expose the scleral wall to the anterior chamber. The device 2 may be used to strip another portion of the trabecular meshwork to expose more of the scleral wall by forming a second terminal opening and advancing the tissue engager 10 to the second terminal opening. The entry opening is created by removing or incising the trabecular meshwork to the outer wall of Schlemm's canal or through Schlemm's canal to expose the sclera. The strip of trabecular meshwork released by the present devices may also be parted off with a separate device or with the devices themselves (by cutting or tearing) as described.

In some implementations, the introducer tube 17 can be rotated relative to the housing 13 using an actuator 25 of the housing 13 (or by rotating the housing 13 itself). Rotation of the tube 17 can direct the tissue engager 10 to access a different band around the eye. For example, the introducer tube 17 can be rotated in a first direction relative to the housing 13 to direct the distal opening 29 from the lumen 19 anteriorly towards the limbus such that advancing the tissue engager 10 can perform a modification of this band of tissue. The introducer tube 17 can be rotated in a second direction relative to the housing 13 to direct the distal opening 29 from the lumen 19 posteriorly towards the ciliary body such that advancing the tissue engager 10 can perform a modification of this band of tissue. The device can also incorporate an actuator configured to move the introducer tube 17 and/or the shaft 6 along the longitudinal axis as well as around the longitudinal axis.

As used herein, the term "displace tissue" includes both blunt engagement to move the tissue but also cutting the tissue to move the tissue in the path of the tissue engager. The terms "gather" tissue and "gathering" tissue means that tissue collects and bunches up in front of or at the tissue engager. The gathered tissue may be somewhat compressed as it collects ahead of the device. Displacement of this gathered tissue advantageously rips/tears/shears the tissue along both lateral sides without cutting at both lateral sides so that a strip of material is being freed from the native tissue. Use of a cutting element may result in a slit being formed without meaningful removal of material. Similarly, use of a rounded tube or element may result in simply tearing the trabecular meshwork open along a seam without meaningful removing material. The ability of the devices described herein to gather tissue does not require the device to gather all of the tissue being removed. The gathered tissue may slide to one side or the other or "over" the tissue engager so that the tissue engager gathering a different part of the trabecular meshwork and tearing/ripping tissue free by displacing the newly gathered different part of the trabecular meshwork. The device can gather tissue corresponding to the width of the tissue engaging element while a rounded tube (or a cutting element) is not capable of gathering tissue in this manner.

The advancing direction as used herein is defined as a local vector that is essentially a tangent to the circular shape of the Schlemm's canal. As such, the advancing direction essentially follows the curvature of the Schlemm's canal rather than defining a single direction. All compatible features of any embodiment shall be interchangeable with any other embodiment and all such combinations are expressly incorporated herein.

In addition, the non-cutting probe and or the tissue micro-disruptor/trabeculorhexis element may both have tissue modulating surface elements on their outer surface that can engage and/or modulate the surface of the external canal wall. For example, such elements may include micro-abrasive surface for canal wall cleaning, debridement and/or thinning. Further embodiments of a combined trabeculorhexis-canaloplasty device whereby in addition to the trabeculorhexis configuration, the device has features designed to change, modulate, abrade, shave, thin, microperforate the outer/external/contralateral-to-the-TM canal wall. This can be achieved by a modified surface architecture of the guide-probe and/or the tissue disruptor and/or the flexible shaft with abrasive non-smooth surface including but not limited to a grating configuration, notching and other surface elements designed to treat and modify the surface the canal wall surface during movement of the device along the contour of the canal. This combined trabeculorhexis-canaloplasty procedure will not only disinsert and remove the TM, but also can improve and change the anatomy of the remaining canal wall for additional improvement of aqueous outflow. In addition, a further embodiment where the surface of such ab-interno device (guide-probe and tissue disruptor) can be coated with a hemostatic coating (e.g. silver nitrate) which can reduce bleeding during the procedure. The simultaneous modification of the inner and outer walls can be performed with a combined device. The method of disrupting the inner and outer walls can also be a two-step method where a first step is performed to modify the trabecular meshwork, for example, with a first device and a second step is performed to modify the outer wall, for example, with a second device. The outer wall modification can occur after the trabecular meshwork modification.

The devices described herein are preferably introduced ab interno but may be practiced with ab externo approach. The device can be moved by advancing to tear tissue, the device may do so preferably without cutting or ablating the tissue. Cutting devices and even a cutting element with the devices may be provided. The method can be performed without any implantable structure (including no implantable structures coupled to the housing) left in the eye or can be performed in conjunction with a shunt or stent-like structure.

As used herein, the terms are often used with reference to a view of the device in use and may be modified as described below to provide further clarification of these term. The term advancing direction may be modified with the term "which is oriented in a tangential direction with respect to the circular shape of the eye." The term height may be modified with the term "which is radially oriented with respect to the circular shape of the eye". Similarly, the term "width" may be modified with the term "which is oriented perpendicular to the advancing direction and the height" or with the term "oriented parallel to a central axis of the eye". Finally, the terms upper or upper surface and lower or lower surface may be modified with the terms "which is oriented on a radially inner surface with respect to the circular shape of the eye" and "oriented on a radially outer surface with respect to the circular shape of the eye", respectively. The above referenced terms apply to circular, tubular and frustoconical shapes equally.

Aspects of the flexible shaft may be used with a cutting or ablating element or the device may be used with a rigid shaft with an articulated head.

Suitable materials or combinations of materials for the preparation of the various components of the devices disclosed herein are provided throughout. It should be appreciated that other suitable materials are considered. The device can be constructed from any implant grade material that can provide the functions required. Materials that may be employed in this device could be but are not limited to nylons, PVDF, PMMA, polyimide, Nitinol, titanium, stainless steel, or other implant grade materials. The device may be made from a combination of materials that are geometrically mated together, chemically bonded or welded to one another, over-molded, encapsulated, or other means for joining multiple materials. A given device element may be made of multiple materials.

The various embodiments described herein incorporate a relatively flexible inner shaft 6 that is extendable from within a stiffer introducer tube 17 to take on the curvature of the eye as it is advanced. The flexible inner shaft 6 simplifies motion of the tool during advancement and disruption. The flexible inner shaft 6 can follow the curved shape of the target tissue without needing to move the distal end of the shaft longitudinally and laterally to follow the curved shape.

The devices described herein may also incorporate straight rigid intraocular shafts that incorporate the tissue engager 10 at a fixed orientation relative to the shaft. The tissue engager 10 may incorporate one or more disruptors 75 positioned near a distal end region of a straight, relatively rigid shaft at an orientation designed to perform outer wall disruption as described elsewhere herein. The tissue disruptor surface and architecture can project radially outward to engage with and modify the outer wall of the canal without "catheterizing" Schlemm's canal. The trabecular meshwork can be removed or disrupted using a first device and a second device used to modify the outer wall now exposed once the trabecular meshwork is disrupted. The device to modify the outer wall can include a proximal handle, an elongate shaft extending distally from the proximal handle, and a tissue engager coupled or formed at a distal end region of the elongate shaft. The elongate shaft can be relatively straight extending along a longitudinal axis from proximal end to distal end and relatively rigid so as not to curve upon entry into the eye. The distal tissue engager can be attached at an angle relative to the distal end region of the elongate shaft in order to make contact with the outer wall of Schlemm's canal from inside the anterior chamber.

The elongate shaft may be formed of materials, such as titanium, stainless steel, or other metal or metal alloys, polyether ether ketone (PEEK), ceramics, rigid plastics, or other materials. The material of the shaft is relatively firm and has the structural ability to exert a force on the outer wall for modification of the outer wall using the disruptor projecting towards the outer wall. The outer wall modification can occur after prior goniotomy with another device or can occur in combination with the goniotomy disruptor using, for example, one or more of the non-catheterized disruptor tools described above. "Catheterize" refers to entering Schlemm's canal for greater than 4 clock hours.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detain in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various placed throughout this specification are not necessarily referring to the same embodiment or implementation. Furthermore, the particular features, structures, configurations, or characteristics may be combined in any suitable manner in one or more implementations.

The devices and systems described herein can incorporate any of a variety of features. Elements or features of one implementation of a device and system described herein can be incorporated alternatively or in combination with elements or features of another implementation of a device and system described herein. For the sake of brevity, explicit descriptions of each of those combinations may be omitted although the various combinations are to be considered herein. Additionally, the devices and systems described herein can be positioned in the eye and need not be implanted specifically as shown in the figures or as described herein. The various devices can be implanted, positioned and adjusted etc. according to a variety of different methods and using a variety of different devices and systems. The various devices can be adjusted before, during as well as any time after implantation. Provided are some representative descriptions of how the various devices may be implanted and positioned, however, for the sake of brevity explicit descriptions of each method with respect to each implant or system may be omitted.

The use of relative terms throughout the description may denote a relative position or direction or orientation and is not intended to be limiting. For example, "distal" may indicate a first direction away from a reference point. Similarly, "proximal" may indicate a location in a second direction opposite to the first direction. Use of the terms "upper," "lower," "top", "bottom," "front," "side," and "back" as well as "anterior," "posterior," "caudal," "cephalad" and the like or used to establish relative frames of reference, and are not intended to limit the use or orientation of any of the devices described herein in the various implementations.

The word "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A device for disrupting tissue in an eye, the device comprising:
   a distal portion sized and configured for ab interno insertion into an anterior chamber of the eye, the distal portion comprising:
   an elongate, flexible shaft of super-elastic memory-shape material comprising:
      a distal end region shaped into a curve having a central plane, wherein a radially inner surface is connected to a radially outer surface by two lateral sides;
      a distal-most end; and
      a tissue disruptor proximal of the distal-most end formed on at least one of the inner surface and the outer surface, wherein the tissue disruptor has a distal face, a proximal face, and a maximum thickness, the distal face sloping from a first thickness of the shaft distal to the tissue disruptor towards the maximum thickness and the proximal face tapering down from the maximum thickness to a second thickness of the shaft proximal to the tissue disruptor, wherein the first thickness, the maximum thickness, and the second thickness are each between the inner and outer surfaces, and
   wherein the distal face of the tissue disruptor is a blunt tissue-engaging surface without any cutting element.

2. The device of claim 1, wherein the distal-most end is a smooth ball tip.

3. The device of claim 2, wherein the smooth ball tip is configured for circumferential gonio-traction.

4. The device of claim 2, wherein the smooth ball tip on the shaft is located 1 mm-3 mm away from the distal face.

5. The device of claim 1, wherein the tissue disruptor comprises a first tissue disruptor formed on the inner surface and a second tissue disruptor formed on or adjacent to the outer surface opposite the first tissue disruptor.

6. The device of claim 1, further comprising a proximal housing having an introducer tube projecting from a distal end region of the housing, at least a portion of the shaft extending through a lumen of the introducer tube.

7. The device of claim 6, wherein the shaft is configured to be advanced from the introducer tube.

8. The device of claim 7, wherein the shaft develops a spring-load as the shaft extends from the introducer tube.

9. The device of claim 7, wherein the shaft applies a radially outward force as the shaft extends from the introducer tube.

10. The device of claim 6, wherein the introducer tube is a substantially rigid tube having a proximal end region that extends away from the proximal housing along a longitudinal axis and a distal end region that curves relative to the longitudinal axis.

11. The device of claim 10, wherein the distal end region of the introducer tube has a first curved region and a second curved region, wherein the first curved region curves in a first direction at a first radius of curvature and the second curved region curves in a second direction at a second radius of curvature.

12. The device of claim 11, wherein the first radius of curvature is greater than the second radius of curvature.

13. The device of claim 1, wherein the first thickness of the shaft between the inner and outer surfaces proximal to the disruptor is 100-2000 microns and the second thickness of the shaft between the inner and outer surfaces distal to the disruptor is 100-550 microns.

14. The device of claim 13, wherein the maximum thickness of the tissue disruptor between the inner and the outer surfaces is about 450-600 microns.

15. The device of claim 1, wherein the shaft has a cross-sectional shape taken transverse to a length of the shaft between that is non-circular.

16. The device of claim 15, wherein the cross-sectional shape is square or rectangular.

17. The device of claim 1, wherein the curve of the distal end region of the shaft has a radial curvature of 5-20 mm.

18. The device of claim 1, wherein the shaft has a length sufficient to be advanced around 30-360 degrees of a circumference of an eye.

* * * * *